US010398688B2

(12) United States Patent
Bassermann et al.

(10) Patent No.: US 10,398,688 B2
(45) Date of Patent: Sep. 3, 2019

(54) METHOD FOR ASSESSING THE EFFICACY OF IMIDS AND COMPOSITION OR COMBINATION FOR USE IN TREATING IMID SENSITIVE DISEASES

(71) Applicant: Klinikum Rechts Der Isar Der TU München, München (DE)

(72) Inventors: Florian Bassermann, München (DE); Ruth Eichner, München (DE); Vanesa Fernandez-Saiz, München (DE)

(73) Assignee: KLINIKUM RECHTS DER ISAR DER TECHNISCHEN UNIVERSITAT MÜNCHEN, MÜNCHEN (DE)

( * ) Notice: Subject to any disclaimer, the term of this patent is extended or adjusted under 35 U.S.C. 154(b) by 0 days.

(21) Appl. No.: 15/513,861

(22) PCT Filed: Sep. 23, 2015

(86) PCT No.: PCT/EP2015/071814
§ 371 (c)(1),
(2) Date: Mar. 23, 2017

(87) PCT Pub. No.: WO2016/046244
PCT Pub. Date: Mar. 31, 2016

(65) Prior Publication Data
US 2017/0296524 A1    Oct. 19, 2017

(30) Foreign Application Priority Data
Sep. 23, 2014 (EP) .................................. 14186016

(51) Int. Cl.
| *A61K 45/06* | (2006.01) |
| *G01N 33/68* | (2006.01) |
| *A61K 31/454* | (2006.01) |
| *A61K 31/713* | (2006.01) |
| *C12N 15/113* | (2010.01) |
| *G01N 33/574* | (2006.01) |

(52) U.S. Cl.
CPC .......... *A61K 31/454* (2013.01); *A61K 31/713* (2013.01); *A61K 45/06* (2013.01); *C12N 15/1138* (2013.01); *G01N 33/57492* (2013.01); *G01N 33/6872* (2013.01); *C12N 2310/14* (2013.01); *C12N 2310/531* (2013.01); *C12N 2320/31* (2013.01); *G01N 2333/705* (2013.01); *G01N 2333/70503* (2013.01); *G01N 2800/52* (2013.01)

(58) Field of Classification Search
CPC ................ A61K 45/06; A61K 2300/00; C12N 15/1138; C12N 2310/14; C12N 2320/31
USPC ........... 424/158.1; 435/6.1, 6.11, 6.12, 6.13, 435/91.1, 91.31; 514/1, 2, 19.3, 44; 536/23.1, 24.31, 24.5
See application file for complete search history.

(56) References Cited

U.S. PATENT DOCUMENTS

| 2009/0028862 A1* | 1/2009 | Arndt ................. C07K 16/2803 424/138.1 |
| 2015/0056215 A1* | 2/2015 | Sukhatme ............ A61K 31/225 424/158.1 |
| 2015/0079590 A1* | 3/2015 | Pandolfi ........... G01N 33/57484 435/6.11 |
| 2018/0002422 A1* | 1/2018 | Freeman ................ C07K 16/28 |

FOREIGN PATENT DOCUMENTS

| EP | 3000479 | 3/2016 |
| WO | 2016046244 | 3/2016 |

OTHER PUBLICATIONS

Broyl et al., High Cereblon Expression is Associated with Better Survival in Patients with Newly Diagnosed Multiple Myeloma Treated with Thalidomide Maintenance, Blood, vol. 121, No. 4, Jan. 24, 2013, pp. 624-627.
European Application No. 14186016.3, Extended European Search Report dated Dec. 1, 2014, 5 pages.
Fernandez-Saiz et al., $SCF^{Fbxo9}$ and CK2 Direct the Cellular Response to Growth Factor Withdrawal Via Tel2/Tti1 Degradation and Promote Survival in Multiple Myeloma, Nature Cell Biology, vol. 15, No. 1, Jan. 2013, pp. 72-81 and 22 pages of supplemental material.
Gandhi et al., Measuring Cereblon as a Biomarker of Response or Resistance to Lenalidomide and Pomalidomide Requires Use of Standardized Reagents and Understanding of Gene Complexity, British Journal of Haematology, vol. 164, No. 2, Jan. 2014, pp. 233-244.
Greenberg et al., Responsiveness of Cytogenetically Discrete Human Myeloma Cell Lines to Lenalidomide: Lack of Correlation with Cereblon and Interferon Regulatory Factor 4 Expression Levels, European Journal of Haematology, vol. 91, No. 6, Dec. 2013, pp. 504-513.
Guile et al., Potent Blockers of the Monocarboxylate Transporter MCT1: Novel Immunomodulatory Compounds, Bioorganic and Medicinal Chemistry Letters, vol. 16, No. 8, Apr. 15, 2006, pp. 2260-2265.

(Continued)

*Primary Examiner* — Jane J Zara
(74) *Attorney, Agent, or Firm* — Kilpatrick Townsend & Stockton LLP

(57) ABSTRACT

The invention relates to a combination of an immunomodulatory imide drug (IMiD) and an inhibitor of CD147 and/or an inhibitor of MCT1 for use in treating a disease in a subject. It further relates to an inhibitor of CD147 and/or an inhibitor of MCT1 for use in treating a disease in a patient, wherein the patient is IMiD resistant. It further relates to a method of monitoring the efficacy of an IMiD treatment regimen by comparing the protein level of CD147 and/or MCT1 in samples obtained from a subject prior and during IMiD treatment.

9 Claims, 22 Drawing Sheets
Specification includes a Sequence Listing.

(56) References Cited

OTHER PUBLICATIONS

Heintel et al., High Expression of Cereblon (CRBN) is Associated with Improved Clinical Response in Patients with Multiple Myeloma Treated with Lenalidomide and Dexamethasone, British Journal of Haematology, vol. 161, No. 5, Jun. 2013, pp. 695-700.

Kronke et al., Lenalidomide causes Selective Degradation of IKZF1 and IKZF3 in Multiple Myeloma Cells, Science Express, available online at http://science.sciencemag.org/content/early/2013/11/27/science.1244851?sid=02f51ef2-0348-4a0a-bb7d-e5ceaa286f81, Nov. 28, 2013, pp. 1-8.

Lu et al., The Myeloma Drug Lenalidomide Promotes the Cereblon-Dependent Destruction of Ikaros Proteins, Science Express, Available online at http://science.sciencemag.org/content/early/2013/11/27/science.1244917?sid=4b105b60-dc51-4c44-90b7-95949594eedd, Nov. 28, 2013, pp. 1-8.

Niu et al., Treatment of $^{131}$I-Labeled Anti-CD147 Monoclonal Antibody in VX2 Carcinoma-Induced Liver Tumors, Oncology Reports, vol. 30, No. 1, Jul. 2013, pp. 246-252.

International Application No. PCT/EP2015/071814, International Preliminary Report on Patentability dated Apr. 6, 2017, 7 pages.

International Application No. PCT/EP2015/071814, International Search Report and Written Opinion dated Nov. 27, 2015, 10 pages.

Schuster et al., The Clinical Significance of Cereblon Expression in Multiple Myeloma, Leukemia Research, vol. 38, No. 1, 2013, pp. 23-28.

Seizer et al., V898—Targeting the Function of EMMPRIN (CD147) Reduces Infarct Size and Preserves Systolic Function After Ischaemia and Reperfusion, Clin Res Cardiol, vol. 99, Suppl. 1, Apr. 2010.

Zhu et al., Cereblon Expression is Required for the Anti-Myeloma Activity of Lenalidomide and Pomalidomide, Blood, vol. 118, No. 18, published online Aug. 22, 2011, pp. 4771-4779.

* cited by examiner

A  MM1s - extracellular lactate 4 days Lenalidomide

B  MM1s - 4 Days Lenalidomide
Intracellular lactate

A

B

```
SEQUENCE LISTING

<160> NUMBER OF SEQ ID NOS: 39

<210> SEQ ID NO 1
<211> LENGTH: 19
<212> TYPE: PRT
<213> ORGANISM: Homo sapiens
<223> OTHER INFORMATION: amino acids 1-19 of human CRBN
<220> FEATURE:
<223> OTHER INFORMATION: amino acids 1-19 of human CRBN

<400> SEQUENCE: 1

Met Ala Gly Glu Asp Gln Gln Asp Ala Ala His Asn Met Gly Asn His
1               5                   10                  15

Leu Pro Cys

<210> SEQ ID NO 2
<211> LENGTH: 15
<212> TYPE: PRT
<213> ORGANISM: Homo sapiens
<223> OTHER INFORMATION: amino acids 424-437 of human CRBN
<220> FEATURE:
<223> OTHER INFORMATION: amino acids 424-437 of human CRBN

<400> SEQUENCE: 2

Cys Pro Thr Ile Asp Pro Thr Glu Asp Glu Ile Ser Pro Asp Lys
1               5                   10                  15

<210> SEQ ID NO 3
<211> LENGTH: 21
<212> TYPE: DNA
<213> ORGANISM: Artificial Sequence
<223> OTHER INFORMATION: "first shRNA target sequence for CRBN"
<220> FEATURE:
<223> OTHER INFORMATION: first shRNA target sequence for CRBN
```

<400> SEQUENCE: 3
cgctggctgt attccttata t                                              21

<210> SEQ ID NO 4
<211> LENGTH: 21
<212> TYPE: DNA
<213> ORGANISM: Artificial Sequence
<223> OTHER INFORMATION: "second shRNA target sequence for CRBN"
<220> FEATURE:
<223> OTHER INFORMATION: second shRNA target sequence for CRBN

<400> SEQUENCE: 4
ccagaaacat ctacttgggt a                                              21

<210> SEQ ID NO 5
<211> LENGTH: 21
<212> TYPE: DNA
<213> ORGANISM: Artificial Sequence
<223> OTHER INFORMATION: "shRNA target sequence for CD147"
<220> FEATURE:
<223> OTHER INFORMATION: shRNA target sequence for CD147

<400> SEQUENCE: 5
gtacaagatc actgactctg a                                              21

<210> SEQ ID NO 6
<211> LENGTH: 21
<212> TYPE: DNA
<213> ORGANISM: Artificial Sequence
<223> OTHER INFORMATION: "shRNA target sequence for MCT1"
<220> FEATURE:
<223> OTHER INFORMATION: shRNA target sequence for MCT1

<400> SEQUENCE: 6
gcagggaaag ataagtctaa a                                              21

<210> SEQ ID NO 7
<211> LENGTH: 21
<212> TYPE: DNA
<213> ORGANISM: Artificial Sequence
<223> OTHER INFORMATION: "shRNA target sequence for IKZF1"
<220> FEATURE:
<223> OTHER INFORMATION: shRNA target sequence for IKZF1

<400> SEQUENCE: 7
ctacgagaag gagaacgaaa t                                              21

<210> SEQ ID NO 8
<211> LENGTH: 21
<212> TYPE: DNA
<213> ORGANISM: Artificial Sequence
<223> OTHER INFORMATION: "shRNA target sequence for IKZF3"
<220> FEATURE:
<223> OTHER INFORMATION: shRNA target sequence for IKZF3

<400> SEQUENCE: 8
gcctgaaatc ccttacagct a                                              21

<210> SEQ ID NO 9
<211> LENGTH: 21
<212> TYPE: RNA
<213> ORGANISM: Artificial Sequence
<223> OTHER INFORMATION: "shRNA target sequence for control sh_scramble"
<220> FEATURE:
<223> OTHER INFORMATION: shRNA target sequence for control sh_scramble

<400> SEQUENCE: 9
cctaaggtta agtcgccctc g                                              21

<210> SEQ ID NO 10
<211> LENGTH: 22
<212> TYPE: DNA
<213> ORGANISM: Artificial Sequence
<223> OTHER INFORMATION: "Primer 1 for CRBN"
<220> FEATURE:
<223> OTHER INFORMATION: Primer 1 for CRBN

<400> SEQUENCE: 10
acagctggtt tcctgggtat gc                                             22

<210> SEQ ID NO 11
<211> LENGTH: 22
<212> TYPE: DNA
<213> ORGANISM: Artificial Sequence
<223> OTHER INFORMATION: "Primer 2 for CRBN"
<220> FEATURE:
<223> OTHER INFORMATION: Primer 2 for CRBN

<400> SEQUENCE: 11
acagagcaga tcgcgttaag cc                                             22

<210> SEQ ID NO 12
<211> LENGTH: 24
<212> TYPE: DNA
<213> ORGANISM: Artificial Sequence
<223> OTHER INFORMATION: "Primer 1 for MCT1"
<220> FEATURE:
<223> OTHER INFORMATION: Primer 1 for MCT1

<400> SEQUENCE: 12
tggctgtcat gtatggtgga ggtc                                           24

<210> SEQ ID NO 13
<211> LENGTH: 22
<212> TYPE: DNA
<213> ORGANISM: Artificial Sequence
<223> OTHER INFORMATION: "Primer 2 for MCT1"
<220> FEATURE:
<223> OTHER INFORMATION: Primer 2 for MCT1

<400> SEQUENCE: 13
gaagctgcaa tcaagccaca gc                                             22

<210> SEQ ID NO 14
<211> LENGTH: 24
<212> TYPE: DNA
<213> ORGANISM: Artificial Sequence
<223> OTHER INFORMATION: "Primer 1 for CD147"
<220> FEATURE:
<223> OTHER INFORMATION: Primer 1 for CD147

<400> SEQUENCE: 14
gatcactgac tctgaggaca aggc                                           24

<210> SEQ ID NO 15
<211> LENGTH: 22
<212> TYPE: DNA
<213> ORGANISM: Artificial Sequence
<223> OTHER INFORMATION: "Primer 2 for CD147"
<220> FEATURE:
<223> OTHER INFORMATION: Primer 2 for CD147

<400> SEQUENCE: 15
tgcgaggaac tcacgaagaa cc                                              22

<210> SEQ ID NO 16
<211> LENGTH: 22
<212> TYPE: DNA
<213> ORGANISM: Artificial Sequence
<223> OTHER INFORMATION: "Primer 1 for ARPP"
<220> FEATURE:
<223> OTHER INFORMATION: Primer 1 for ARPP

<400> SEQUENCE: 16
gcactggaag tccaactact tc                                              22

<210> SEQ ID NO 17
<211> LENGTH: 22
<212> TYPE: DNA
<213> ORGANISM: Artificial Sequence
<223> OTHER INFORMATION: "Primer 2 for ARPP"
<220> FEATURE:
<223> OTHER INFORMATION: Primer 2 for ARPP

<400> SEQUENCE: 17
tgaggtcctc cttggtgaac ac                                              22

<210> SEQ ID NO 18
<211> LENGTH: 25
<212> TYPE: DNA
<213> ORGANISM: Artificial Sequence
<223> OTHER INFORMATION: "splice morpholino for CD147"
<220> FEATURE:
<223> OTHER INFORMATION: splice morpholino for CD147

<400> SEQUENCE: 18
aagaggtgaa gaacatacaa gtgtt                                           25

<210> SEQ ID NO 19
<211> LENGTH: 16
<212> TYPE: PRT
<213> ORGANISM: Artificial Sequence
<223> OTHER INFORMATION: "CD147 fragment"
<220> FEATURE:
<223> OTHER INFORMATION: CD147 fragment

<400> SEQUENCE: 19

Lys Gly Gly Val Val Leu Lys Glu Asp Ala Leu Pro Gly Gln Lys Thr
1               5                   10                  15

<210> SEQ ID NO 20
<211> LENGTH: 10
<212> TYPE: PRT
<213> ORGANISM: Artificial Sequence
<223> OTHER INFORMATION: "CD147 fragment"
<220> FEATURE:
<223> OTHER INFORMATION: CD147 fragment

<400> SEQUENCE: 20

Lys Glu Asp Ala Leu Pro Gly Gln Lys Thr
1               5                   10

<210> SEQ ID NO 21
<211> LENGTH: 18
<212> TYPE: PRT
<213> ORGANISM: Artificial Sequence
<223> OTHER INFORMATION: "CD147 fragment"
<220> FEATURE:
<223> OTHER INFORMATION: CD147 fragment
<220> FEATURE:

```
<221> NAME/KEY: MOD_RES
<222> LOCATION: 16
<223> OTHER INFORMATION: Cysteine modified by carbamidomethylation (+57)

<400> SEQUENCE: 21

Lys Ser Ser Glu His Ile Asn Glu Gly Glu Thr Ala Met Leu Val Cys
1               5                   10                  15

Lys Ser

<210> SEQ ID NO 22
<211> LENGTH: 16
<212> TYPE: PRT
<213> ORGANISM: Artificial Sequence
<223> OTHER INFORMATION: "CD147 fragment"
<220> FEATURE:
<223> OTHER INFORMATION: CD147 fragment

<400> SEQUENCE: 22

Lys Ser Glu Ser Val Pro Pro Val Thr Asp Trp Ala Trp Tyr Lys Ile
1               5                   10                  15

<210> SEQ ID NO 23
<211> LENGTH: 11
<212> TYPE: PRT
<213> ORGANISM: Artificial Sequence
<223> OTHER INFORMATION: "CD147 fragment"
<220> FEATURE:
<223> OTHER INFORMATION: CD147 fragment

<400> SEQUENCE: 23

Arg Phe Phe Val Ser Ser Ser Gln Gly Arg Ser
1               5                   10

<210> SEQ ID NO 24
<211> LENGTH: 20
<212> TYPE: PRT
<213> ORGANISM: Artificial Sequence
<223> OTHER INFORMATION: "CD147 fragment"
<220> FEATURE:
<223> OTHER INFORMATION: CD147 fragment
<220> FEATURE:
<221> NAME/KEY: MOD_RES
<222> LOCATION: 11
<223> OTHER INFORMATION: oxidation of methionine (+16)

<400> SEQUENCE: 24

Arg Ser Glu Leu His Ile Glu Asn Leu Asn Met Glu Ala Asp Pro Gly
1               5                   10                  15

Gln Tyr Arg Cys
            20

<210> SEQ ID NO 25
<211> LENGTH: 12
<212> TYPE: PRT
<213> ORGANISM: Artificial Sequence
<223> OTHER INFORMATION: "CD147 fragment"
<220> FEATURE:
<223> OTHER INFORMATION: CD147 fragment

<400> SEQUENCE: 25

Lys Gly Ser Asp Gln Ala Ile Ile Thr Leu Arg Val
1               5                   10

<210> SEQ ID NO 26
<211> LENGTH: 20
<212> TYPE: PRT
<213> ORGANISM: Artificial Sequence
```

<223> OTHER INFORMATION: "CD147 fragment"
<220> FEATURE:
<223> OTHER INFORMATION: CD147 fragment

<400> SEQUENCE: 26

Arg Arg Lys Pro Glu Asp Val Leu Asp Asp Asp Ala Gly Ser Ala
1               5                   10                  15

Pro Leu Lys Ser
            20

<210> SEQ ID NO 27
<211> LENGTH: 9
<212> TYPE: PRT
<213> ORGANISM: Artificial Sequence
<223> OTHER INFORMATION: "MCT1 fragment"
<220> FEATURE:
<223> OTHER INFORMATION: MCT1 fragment

<400> SEQUENCE: 27

Lys Ser Ile Thr Val Phe Phe Lys Glu
1               5

<210> SEQ ID NO 28
<211> LENGTH: 17
<212> TYPE: PRT
<213> ORGANISM: Artificial Sequence
<223> OTHER INFORMATION: "MCT1 fragment"
<220> FEATURE:
<223> OTHER INFORMATION: MCT1 fragment

<400> SEQUENCE: 28

Lys Asp Leu His Asp Ala Asn Thr Asp Leu Ile Gly Arg His Pro Lys
1               5                   10                  15

Gln

<210> SEQ ID NO 29
<211> LENGTH: 14
<212> TYPE: PRT
<213> ORGANISM: Artificial Sequence
<223> OTHER INFORMATION: "MCT1 fragment"
<220> FEATURE:
<223> OTHER INFORMATION: MCT1 fragment

<400> SEQUENCE: 29

Lys Asp Leu His Asp Ala Asn Thr Asp Leu Ile Gly Arg His
1               5                   10

<210> SEQ ID NO 30
<211> LENGTH: 11
<212> TYPE: PRT
<213> ORGANISM: Artificial Sequence
<223> OTHER INFORMATION: "MCT1 fragment"
<220> FEATURE:
<223> OTHER INFORMATION: MCT1 fragment

<400> SEQUENCE: 30

Arg Leu Asn Asp Met Tyr Gly Asp Tyr Lys Tyr
1               5                   10

<210> SEQ ID NO 31
<211> LENGTH: 23
<212> TYPE: PRT
<213> ORGANISM: Artificial Sequence
<223> OTHER INFORMATION: "MCT1 fragment"
<220> FEATURE:
<223> OTHER INFORMATION: MCT1 fragment

```
<400> SEQUENCE: 31

Lys Lys Glu Ser Lys Glu Glu Glu Thr Ser Ile Asp Val Ala Gly Lys
1               5                   10                  15

Pro Asn Glu Val Thr Lys Ala
            20

<210> SEQ ID NO 32
<211> LENGTH: 22
<212> TYPE: PRT
<213> ORGANISM: Artificial Sequence
<223> OTHER INFORMATION: "MCT1 fragment"
<220> FEATURE:
<223> OTHER INFORMATION: MCT1 fragment

<400> SEQUENCE: 32

Lys Glu Ser Lys Glu Glu Glu Thr Ser Ile Asp Val Ala Gly Lys Pro
1               5                   10                  15

Asn Glu Val Thr Lys Ala
            20

<210> SEQ ID NO 33
<211> LENGTH: 21
<212> TYPE: DNA
<213> ORGANISM: Artificial Sequence
<223> OTHER INFORMATION: "shRNA target sequence for CUL4A"
<220> FEATURE:
<223> OTHER INFORMATION: shRNA target sequence for CUL4A

<400> SEQUENCE: 33
gcagaactga tcgcaaagca t                                         21

<210> SEQ ID NO 34
<211> LENGTH: 21
<212> TYPE: DNA
<213> ORGANISM: Artificial Sequence
<223> OTHER INFORMATION: "shRNA target sequence for CUL4B"
<220> FEATURE:
<223> OTHER INFORMATION: shRNA target sequence for CUL4B

<400> SEQUENCE: 34
gccatgaaag aagcatttga a                                         21

<210> SEQ ID NO 35
<211> LENGTH: 34
<212> TYPE: DNA
<213> ORGANISM: Artificial Sequence
<223> OTHER INFORMATION: "Primer for CD147 exon 3"
<220> FEATURE:
<223> OTHER INFORMATION: Primer for CD147 exon 3

<400> SEQUENCE: 35
aggccactat tgggtcaaga atggaaagaa aatc                           34

<210> SEQ ID NO 36
<211> LENGTH: 28
<212> TYPE: DNA
<213> ORGANISM: Artificial Sequence
<223> OTHER INFORMATION: "Primer for CD147 exon 5"
<220> FEATURE:
<223> OTHER INFORMATION: Primer for CD147 exon 5

<400> SEQUENCE: 36
ccgttctcct gcatcaggaa gcttgaac                                  28

<210> SEQ ID NO 37
```

```
<211> LENGTH: 21
<212> TYPE: DNA
<213> ORGANISM: Artificial Sequence
<223> OTHER INFORMATION: "Primer 1 for beta-actin"
<220> FEATURE:
<223> OTHER INFORMATION: Primer 1 for beta-actin

<400> SEQUENCE: 37
tgttttcccc tccattgttg g                                                        21

<210> SEQ ID NO 38
<211> LENGTH: 20
<212> TYPE: DNA
<213> ORGANISM: Artificial Sequence
<223> OTHER INFORMATION: "Primer 2 for beta-actin"
<220> FEATURE:
<223> OTHER INFORMATION: Primer 2 for beta-actin

<400> SEQUENCE: 38
ttctccttga tgtcacggac                                                          20

<210> SEQ ID NO 39
<211> LENGTH: 25
<212> TYPE: DNA
<213> ORGANISM: Artificial Sequence
<223> OTHER INFORMATION: "splice morpholino for CD147 ATG"
<220> FEATURE:
<223> OTHER INFORMATION: splice morpholino for CD147 ATG

<400> SEQUENCE: 39
gcgccaaaga gcttcttttc catgc                                                    25
```

METHOD FOR ASSESSING THE EFFICACY OF IMIDS AND COMPOSITION OR COMBINATION FOR USE IN TREATING IMID SENSITIVE DISEASES

CROSS REFERENCE TO RELATED APPLICATIONS

The present application claims priority to EP Application No. 14186016.3, filed Sep. 23, 2014, which is hereby incorporated herein by reference in its entirety.

FIELD OF THE INVENTION

The invention is concerned with an agent or a combination of agents that is useful for treating a disease associated with overexpression of CD147 and/or MCT1, such as cancer or premalignant conditions, in particular hematological cancers, such as multiple myeloma (MM), and with a method of assessing the efficacy of IMiDs in treating said disease or condition and/or assessing IMiD-resistance in cells or in a patient.

BACKGROUND

Hematological malignancies are malignant neoplasms also termed "blood cancer". Hematological malignancies may derive from either of the myeloid or the lymphoid cell line. The myeloid cell line normally produces granulocytes, erythrocytes, thrombocytes, macrophages and mast cells; the lymphoid cell line produces B, T, NK and plasma cells. Lymphomas, lymphocytic leukemias, and myeloma are from the lymphoid line, while acute and chronic myelogenous leukemia, myelodysplastic syndromes and myeloproliferative diseases are myeloid in origin.

Established treatments of hematological malignancy include administration of immunomodulatory imide drugs (IMiDs) to the subject. IMiDs are a defined group of compounds that comprises thalidomide and analogues of thalidomide (α-N-phthalimido-glutarimide), a glutamic acid derivative with anti-angiogenic, anti-proliferative, and immunomodulatory properties. Thalidomide analogues were initially synthesized with the aim of optimizing anti-angiogenic, anti-proliferative, and immunomodulatory properties while reducing toxicities. Several IMiD compounds, such as lenalidomide and pomalidomide, are currently the subject of extensive clinical evaluation in hematological malignancies. IMiDs have been successfully used in the treatment of multiple myeloma and other hemato-oncological diseases for some years.

In particular, treatment with IMiDs is among the established standard therapies for multiple myeloma and has led to a significant improvement in overall survival. Furthermore, IMiDs have been approved for the treatment of mantle cell lymphoma as well as the del(5q) variant of the myelodysplastic syndrome (MDS). A large number of clinical studies have demonstrated efficacy in the treatment of other hematologic malignancies such as chronic lymphocytic leukemia (CLL) or diffuse large B-cell lymphoma. In addition, there is increasing evidence for the efficacy of IMiDs on some non-hematologic neoplasms such as hepatocellular or prostate cancer. However, IMiDs are not always therapeutically active, because many patients develop resistance after initial clinical response, while some patients are resistant upfront. Given also the severe side effects accompanying and caused by the IMiD treatment, there is a need for a method for assessing the efficacy of an IMiD for use in therapeutic treatment before administration to a patient and for monitoring the efficacy of an IMiD over the course of the treatment. Therefore it was one object of the present invention to provide a method for assessing the efficacy of IMiDs in treatment of a malignant or premalignant disease or condition, such as hematological and non-hematological malignancies. There is also a need for the provision of an alternative treatment regimen to the IMiD treatment, wherein the subject to be treated has been identified as being resistant to IMiD treatment.

Despite the increasing clinical use, the molecular mechanisms that lead to the immunomodulatory, anti-angiogenic, anti-inflammatory and anti-proliferative effects of IMiDs have been unclear. Only recently, a direct molecular interactor of IMiDs named Cereblon (CRBN) has been identified. The expression of CRBN is essential for the effectiveness of IMiDs, and is crucial for both the teratotoxic as well as the anti-proliferative and immunomodulatory effects of IMiDs.

CRBN is described to be a DCAF (DDB1-CUL4-associated factor), which together with the scaffold protein CUL4, the Cullin adapter DDB1, and the E2 ligase binding RING domain protein ROC1 forms a functional E3 ubiquitin ligase complex of the CRL4 (Cullin4-Ring ligase) family. DCAFs act as the substrate-specific part of the CRL4 E3 ligases, which ubiquitinate various substrate proteins. The specific binding of substrates leads to the ubiquitination by $CRL4^{CRBN}$ ligase. Depending on the number of linked ubiquitin molecules and type of linkage there are mono-, multiple mono- or polyubiquitinations via lysine K6, K11, K27, K29, K33, K48 or K63, which each have different effects on the fate of the substrate. While K48 and K11-linked polyubiquitinations typically lead to proteasomal degradation, the remaining ubiquitinations rather determine non proteolytical fates of a protein (e.g. binding to other proteins or subcellular localization and protein trafficking). However, there are also E3 ligase components for which non-ligase functions have been described.

CRBN has been identified as a molecular interactor of IMiDs, but the cellular function of CRBN remains largely unclear. Notably, the two B-cell specific transcription factors IZKF1 and IZKF3 have recently been identified as substrates of CRBN, which are only targeted for proteasomal degradation upon treatment with IMiDs. While some immunomodulatory effects of IMiDs like modified IL2 secretion may be explained by the degradation of IZKF1 and IZKF3, the anti-proliferative, anti-angiogenic but also teratotoxic effects remain functionally unclear. Given the B-cell specific expression of IZKF1 and IZKF3, the efficacy of IMiDs in other malignancies like MDS cannot be explained. Moreover, no clear correlation between the expression or degradation of IZKF1 and IZKF3 due to IMiD treatment and the efficacy of the IMiD sensitivity of the cell lines was evident, thus limiting their application as predictive markers [1, 2].

Therefore, questions about the precise molecular mechanism of action of IMiDs, about parameters that predict therapeutic response, or about alternative therapeutic target structures were still unanswered. Although in several studies it has been tried to find a correlation of CRBN expression with the response to IMiD therapy, particularly in the therapy of multiple myeloma, the results were not conclusive. One study showed a correlation between CRBN expression at the protein level with the IMiD sensitivity of myeloma cell lines [3], while other studies have failed to demonstrate this relationship [4, 5]. Similar inconclusive results were shown when assessing CRBN mRNA levels in patient samples [6-8]. These contradictory results could be due, at least in part, to a lack of correlation between mRNA and protein expression levels as well as to a variety of different splice variants of CRBN which complicate a standardized diagnostic.

In summary it can be stated that the CRBN expression level (protein and/or mRNA) could be a potential predictive marker for the efficacy of IMiDs. This has, however, to be further examined due to the high complexity of the not yet understood molecular mechanisms involved. For example, as some myeloma cell lines are IMiD resistant despite exhibiting a high expression of wild-type CRBN, it is contemplated that other factors besides the CRBN expression alone could be responsible for the efficacy of IMiD treatment regimens.

(A): HEK 293T cells were transfected with plasmids coding for Strep-Flag tagged CRBN (CRBN-SF), non-tagged CRBN (CRBN) or empty vector (EV) as control and harvested 24 h later. After lysis of the cells, a first purification was done using Streptavidin beads followed by a second immunoprecipitation using Flag beads. 5% of the purified and eluted protein sample was separated by SDS-PAGE and visualized by silver staining.

(B): Mass spectrometry analysis of protein samples resulted in a list of potential CRBN interactors, including DDB1 and Cul4 as components of the CRL4-E3 ubiquitin ligase, as well as CD147 and MCT1 as previously unknown interactors. The molecular weight in kDa as well as the number of identified peptides in the different samples are specified.

Figure 2:
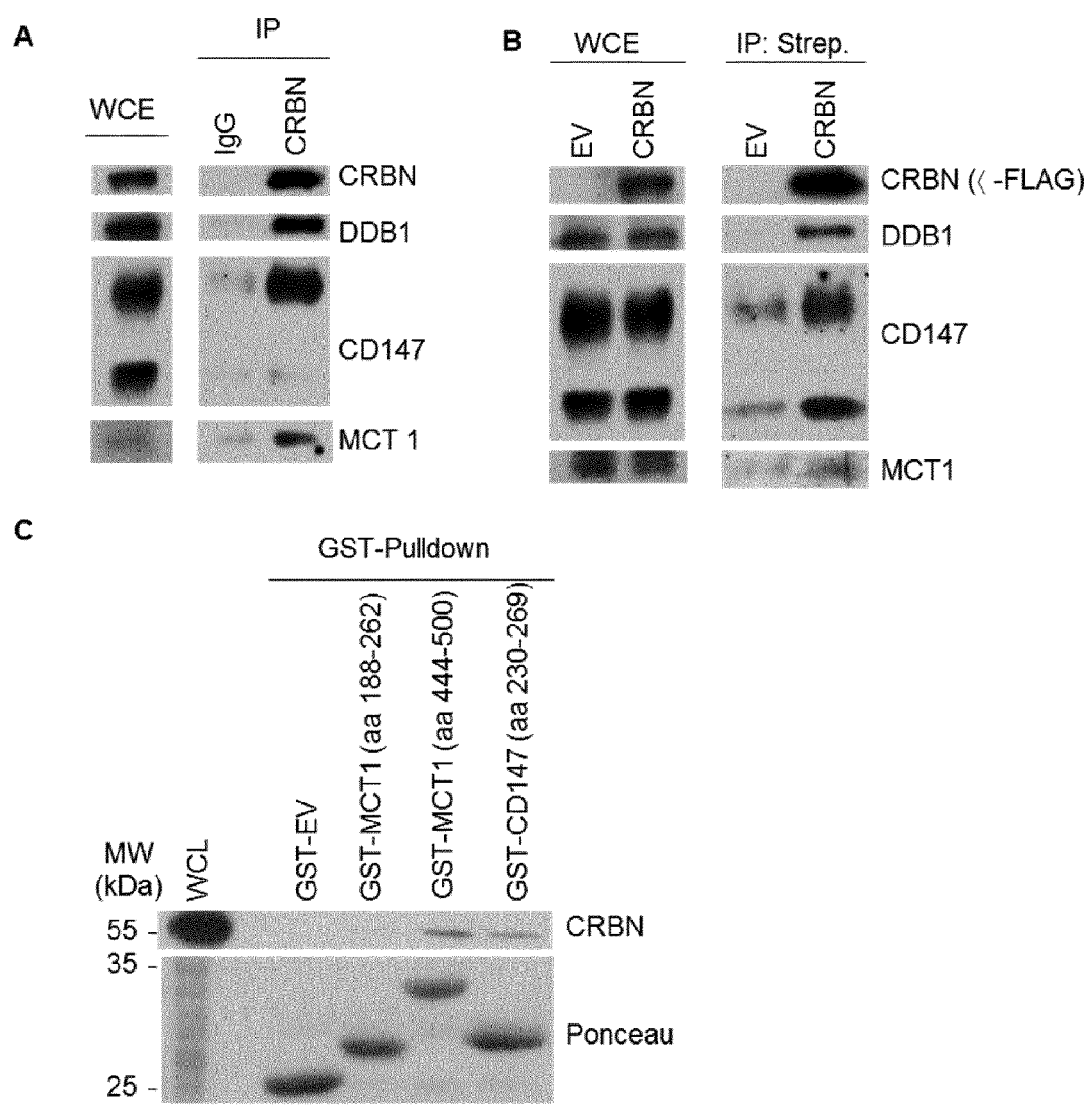

FIG. 2 shows that CD147 and MCT1 interact with CRBN.

(A): CD147 and MCT1 co-immunoprecipitate with endogenous CRBN. Unmodified HEK 293T cells were lysed and incubated with CRBN-specific or control IgG-antibody together with Protein A beads. The immunoprecipitated samples were separated by SDS-PAGE, blotted and incubated with the antibodies against the specified proteins.

(B): Overexpressed CRBN interacts with CD147 and MCT1.
HEK 293T cells were transfected with Strep-Flag tagged CRBN or empty vector (EV) control. After 24 h, the cells were lysed and CRBN was immunoprecipitated using Streptavidin beads.

(C): The intracellular C-terminal domains of MCT1 and CD147 interact with CRBN. The intracellular protein domains of MCT1 (intracellular loop in middle of protein: amino acids 188-262 and C-terminal domain: amino acids 444-500) and CD147 (C-terminal domain: amino acids 230-269) were expressed with GST-tags in bacteria and purified with Glutathion-Sepharose beads. The beads with the purified protein fragments were incubated with whole cell lysate (WCL) from MM1. S cells, spinned down and washed repeatedly, before they were examined for CRBN binding via Western Blot.

Figure 3:
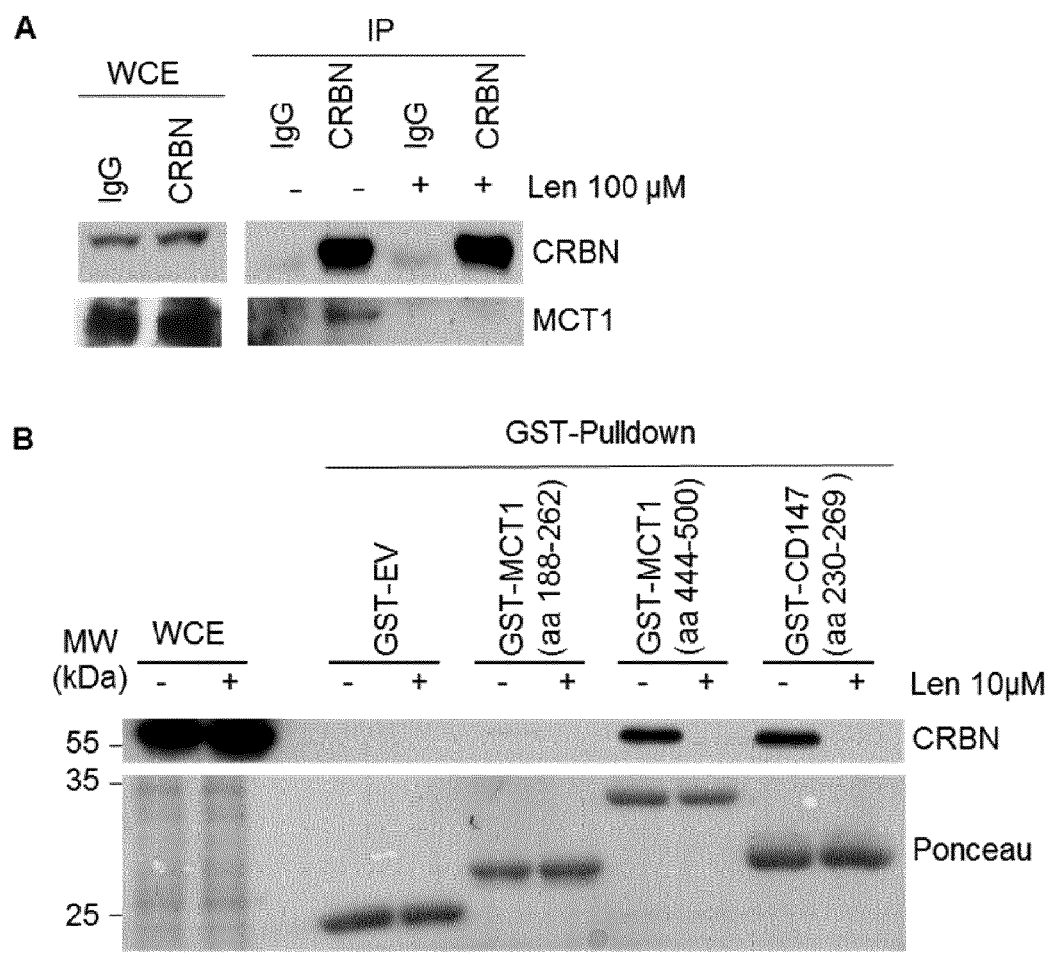

FIG. 3 shows that IMiDs inhibit binding of CRBN to CD147 and MCT1.

(A): HEK 293T cells were incubated with lenalidomide for 24 h in the specified concentration. After lysis, immunoprecipitations were performed using anti-CRBN or anti-IgG control antibodies; the binding of MCT1 was evaluated by Western Blot.

(B): Glutathion-sepharose beads with GST-tagged intracellular protein domains of MCT1 and CD147 (see FIG. 2C) were incubated with whole cell lysate (WCL) from MM1. S cells, which have been treated with lenalidomide or DMSO for 48 hours. The GST-pulldowns were performed in presence or absence of lenalidomide. The beads were spinned down and washed repeatedly, before they were examined for CRBN binding via Western Blot.

Figure 4:
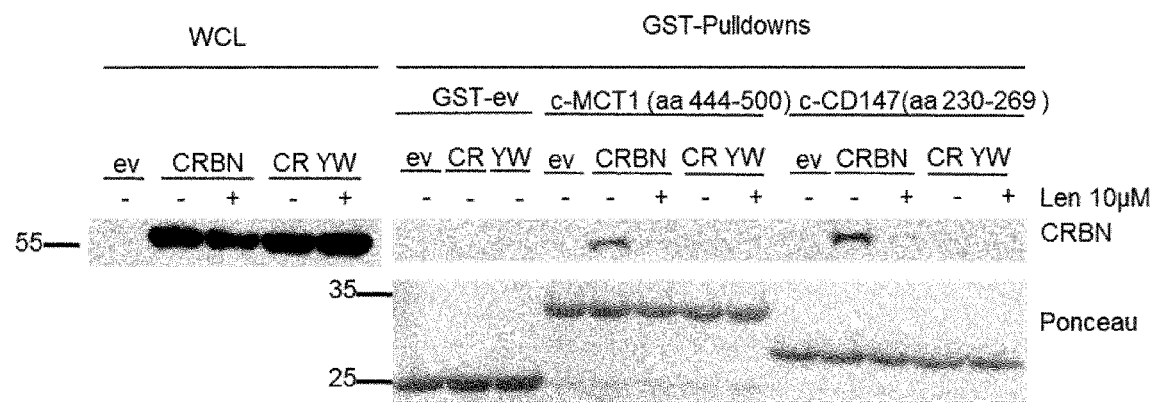

FIG. 4 shows that CRBN binds MCT1 and CD147 at its IMiD-binding pocket.

CRBN−/− HEK 293T cells were transfected with expression plasmids coding for wildtype CRBN (CRBN) or the IMiD-binding defective mutant CRBN Y384A/W386A (CR YW), in which the IMiD binding pocket is misfolded. After transfection, cells were treated with lenalidomide in the indicated concentration or DMSO for 48 hours. The harvested cells were lysed and GST pulldowns with the previously described GST-tagged fragments of the C-terminus of CD147 or MCT1 were performed (see FIGS. 2C and 3B). Binding of CRBN or CRBN YW was evaluated by Western Blot.

Figure 5:
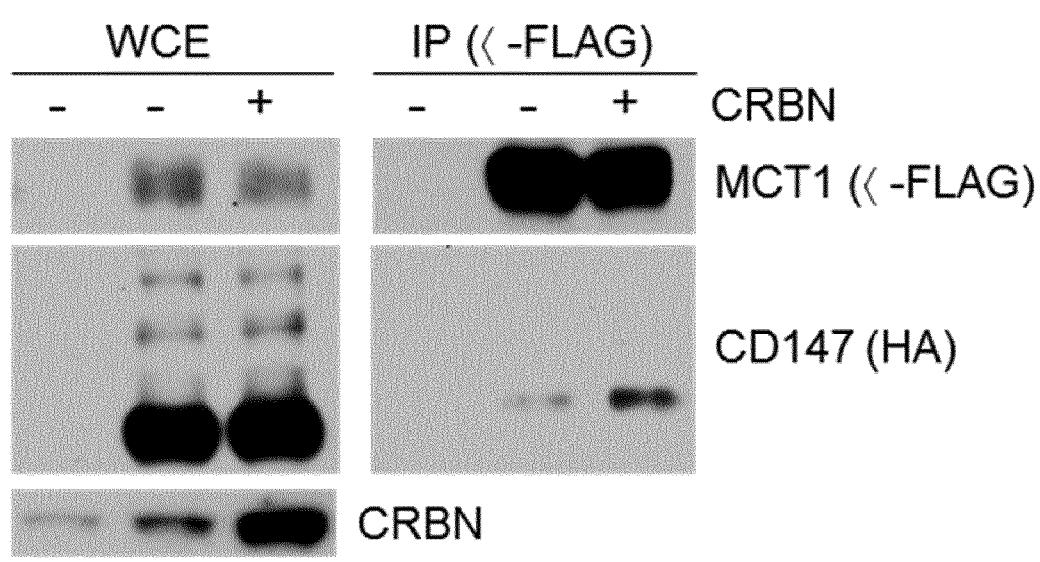

FIG. 5 shows that CRBN enhances interaction of CD147 and MCT1.

HEK 293T cells were transfected with Flag-tagged MCT1, HA-CD147 and CRBN or empty vector control. After lysis, MCT1 was immunoprecipitated with Flag-beads. Binding to CD147 was analysed by Western Blot.

Figure 6:
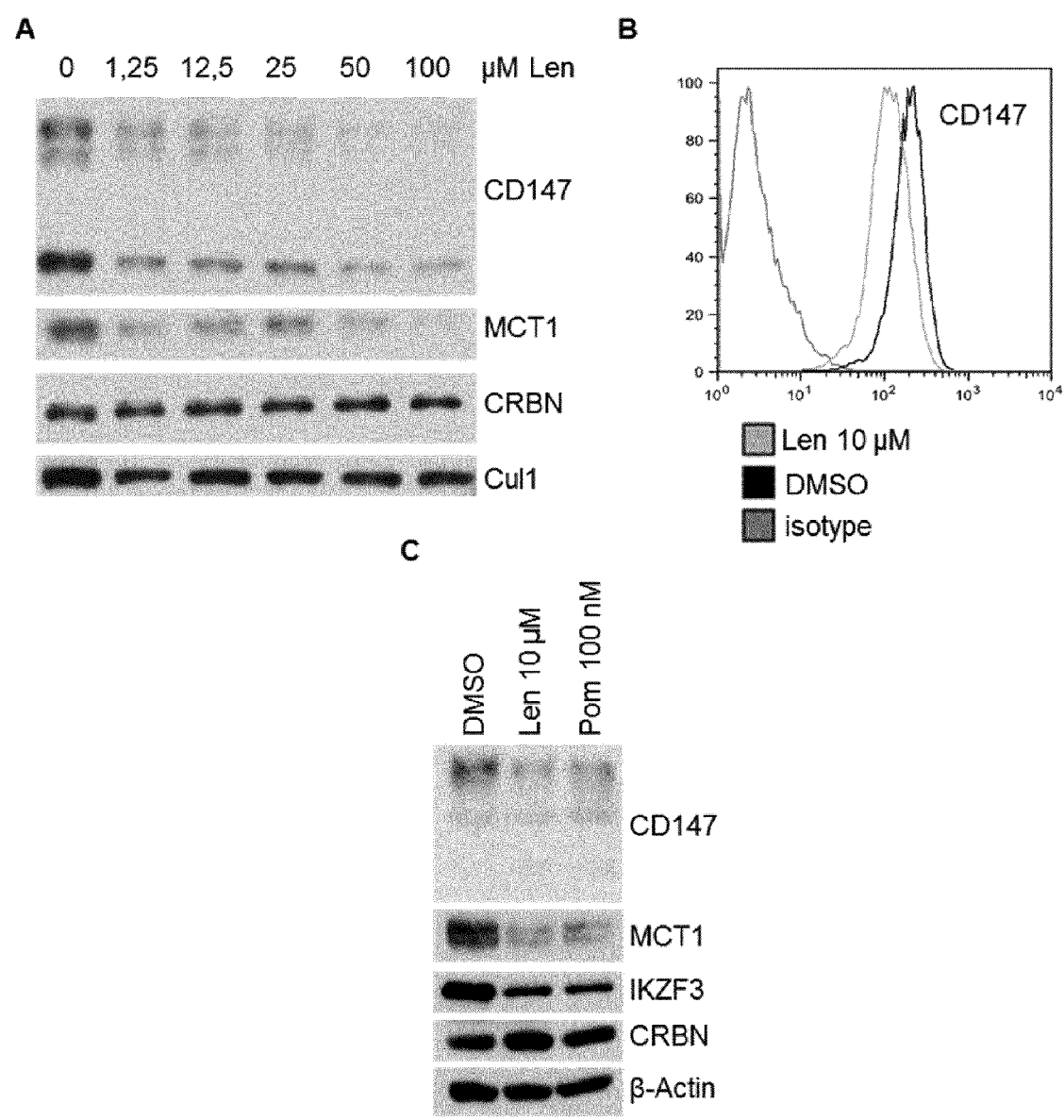

FIG. 6 shows that IMiD treatment leads to a dose-dependent destabilization of CD147 and MCT1 in myeloma cells.

(A): MM1. S cells were treated with lenalidomide in the indicated concentrations for 72 h and then harvested. Abundance of the indicated proteins in whole cell lysates was evaluated by Western Blot.

(B): MM1. S cells were treated with lenalidomide for 72 h and subsequently incubated with anti-CD147 or control IgG antibody and analysed by flow cytometry.

(C): Lenalidomide and pomalidomide have similar effects on CD147 and MCT1 levels. MM1. S cells were treated with lenalidomide or pomalidomide in the indicated concentration. Western Blots of whole cell lysates are shown.

Figure 7:
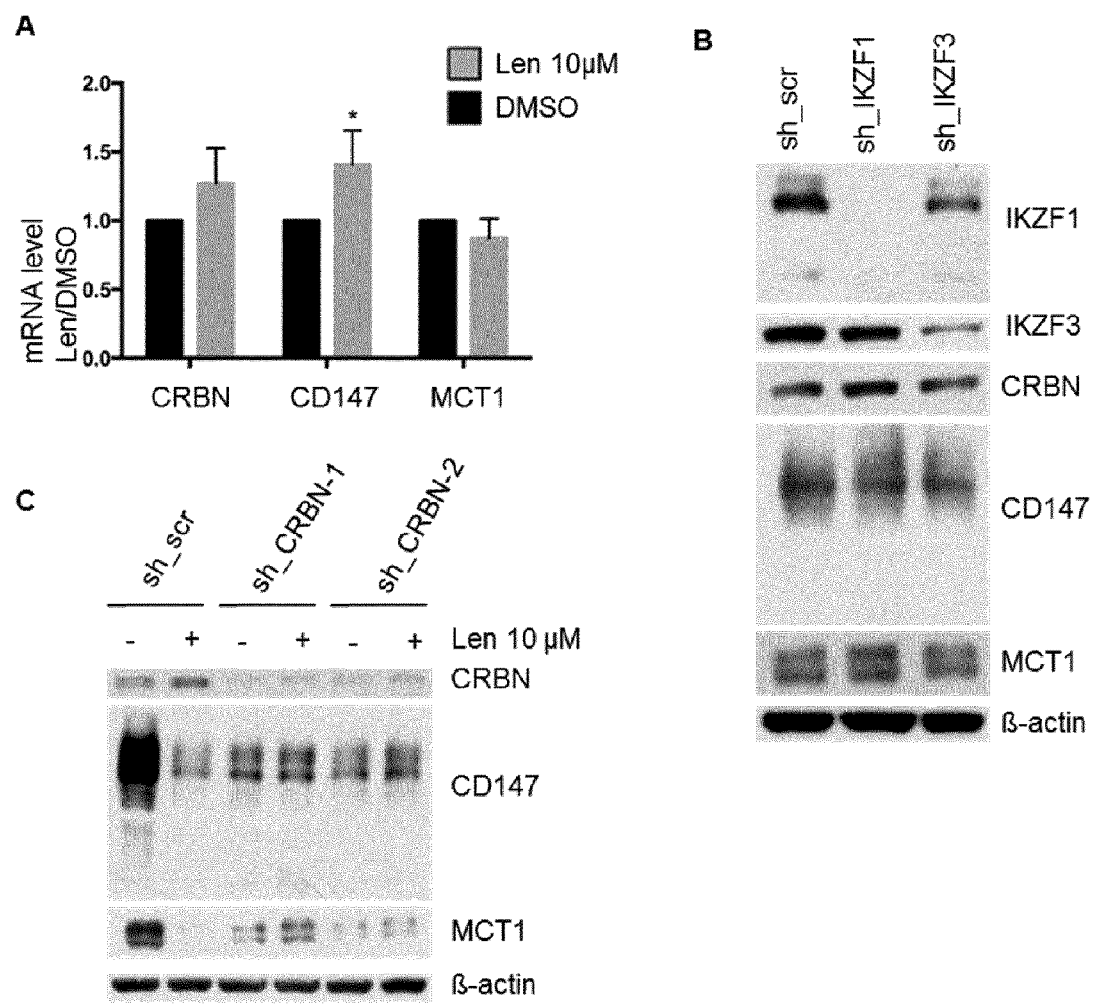

FIG. 7 shows that the IMiD induced destabilization of CD147 and MCT1 occurs on a post-translational level and depends on CRBN but not on IKZF1 or IKZF3.

(A): Transcriptional levels of CRBN, CD147 and MCT1 do not decrease after IMiD treatment.
MM1. S cells were treated with lenalidomide 10 μM or DMSO for 72 h, after harvest, mRNA was isolated. After reverse transcription, qPCR was performed with primers specific for CRBN, CD147 and MCT1.

(B): MM1. S cells were infected with lentiviral particles coding for shRNAs specific for IKZF1 or IKZF3 (or sh_scramble as control), harvested and blotted for the proteins indicated.

(C): MM1. S cells were infected with lentiviral particles coding for shRNAs specific for CRBN (or sh_scramble as control) and treated with lenalidomide 10 μM or DMSO for 4 days. Whole cell lysates were analysed by Western Blot for abundance of the indicated proteins.

Figure 8:
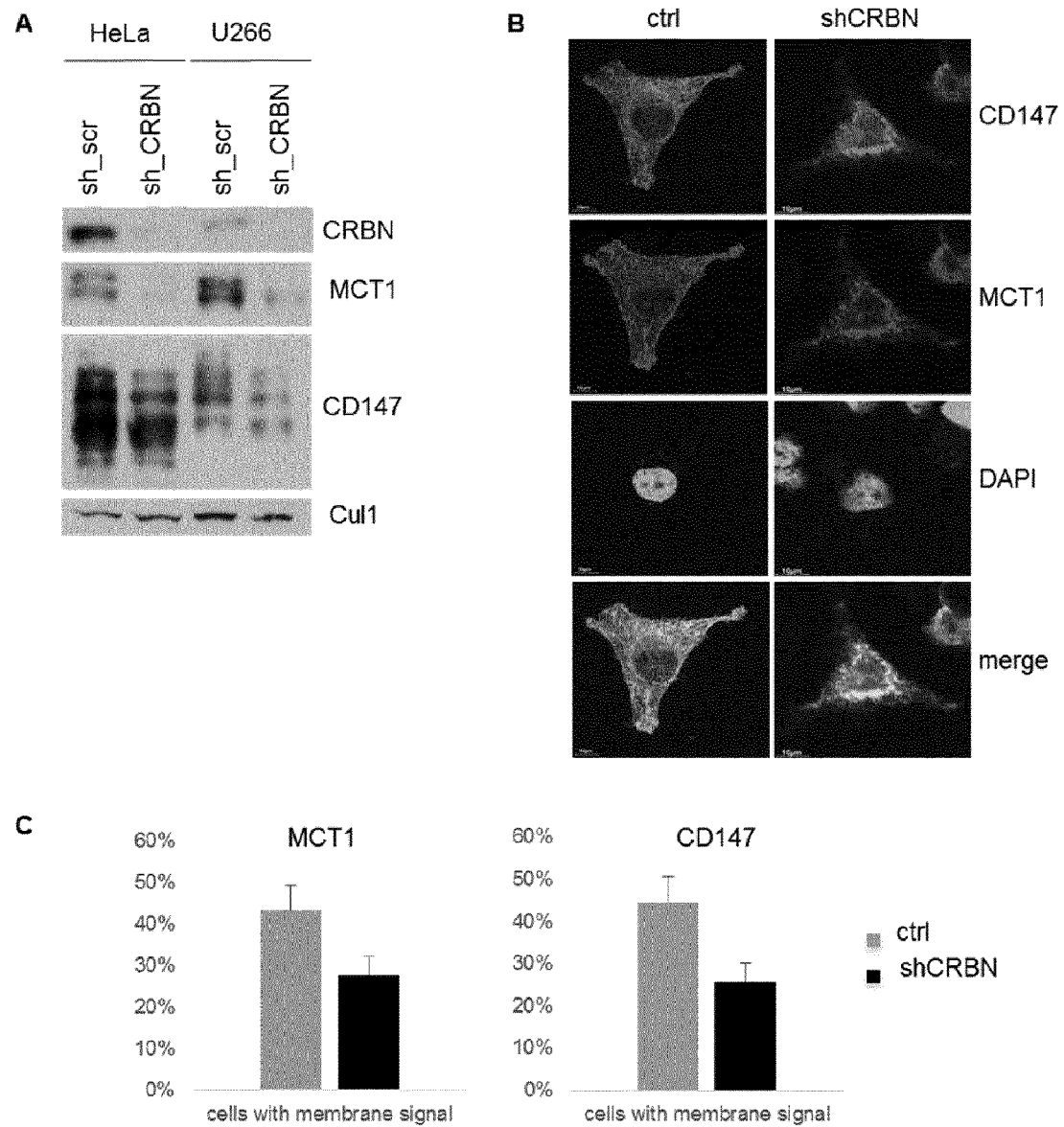

FIG. 8 shows that knockdown of CRBN leads to destabilization and reduced membrane localization of MCT1 and CD147.

(A): HeLa cells and U266 myeloma cells were infected with lentiviral particles coding for shRNAs against CRBN or scramble and harvested 10 days after infection. Whole cell lysates were analyzed by Western Blot.

(B): HeLa cells stably expressing sh_CRBN or sh_scramble were transfected with plasmids coding for HA-CD147 and Flag-MCT1. The transfected cells were fixed and incubated with primary antibodies against Flag or HA, and subsequently with secondary antibodies coupled with fluorochromes. Representative images of the predominant phenotype are shown.

(C): Quantification of membrane localization of CD147 and MCT1 within the experiment described in (B). 100 cells were counted per condition.

Figure 9:
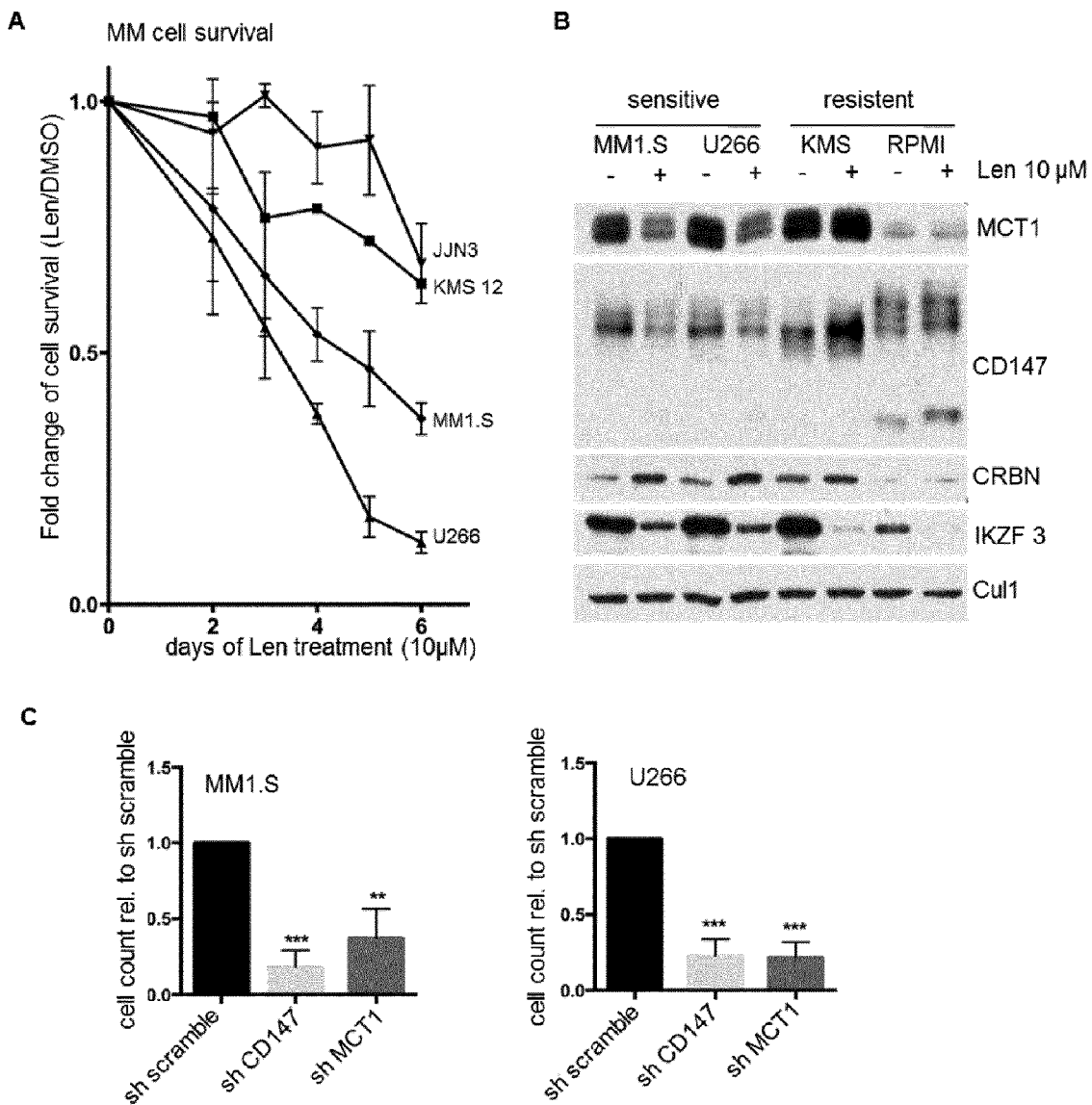

FIG. 9 shows that IMiD treatment leads to destabilisation of MCT1 and CD147 only in IMiD-sensitive myeloma cell lines, thereby contributing to the anti-myeloma effect.

(A): Survival of different myeloma cell lines after lenalidomide treatment.

The MM cell lines MM1. S, U266, JJN3 and KMS-12-BM were treated with 10 μM lenalidomide or DMSO; the surviving cells were counted each day using the trypan blue exclusion method.

(B): The IMiD-sensitive cell lines MM1. S and U266 and the two largely IMiD-resistant cell lines RPMI and KMS-12-BM were treated with the indicated concentrations of lenalidomide for 72 hours. Whole cell lysates were analysed for protein abundance by Western Blot.

(C): Knockdown of CD147 and MCT1 inhibits myeloma cell growth and leads to apoptosis.

MM1. S and U266 myeloma cell lines were infected with lentiviral particles coding for shRNA against CD147 or MCT1 or sh_scramble as control. Survival of the infected cells was analyzed on day 6 after infection. Cell counts are depicted relative to sh_scramble.

Figure 10:
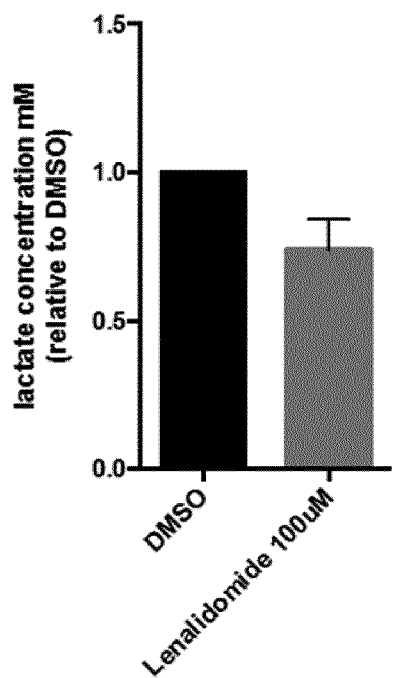
Figure 10:
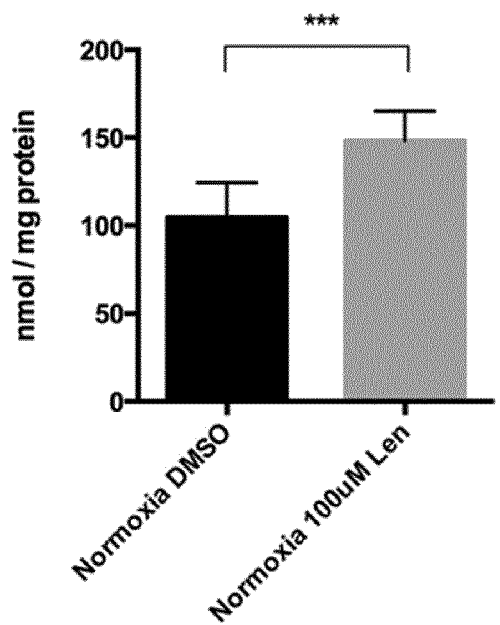

FIG. 10 shows that IMiD-induced destabilization of MCT1 leads to reduced cellular lactate export.

MM1. S cells were treated with lenalidomide in the indicated concentration or with DMSO for 4 days.

(A): After spinning down the cells, aliquots of the supernatant were taken for extracellular lactate measurement.

(B): The harvested cell pellets were lysed in lysis buffer. Intracellular lactate levels were determined within the whole cell lysates. To determine lactate content per amount of protein within the cells, the protein concentration of each sample was also measured.

Figure 11:
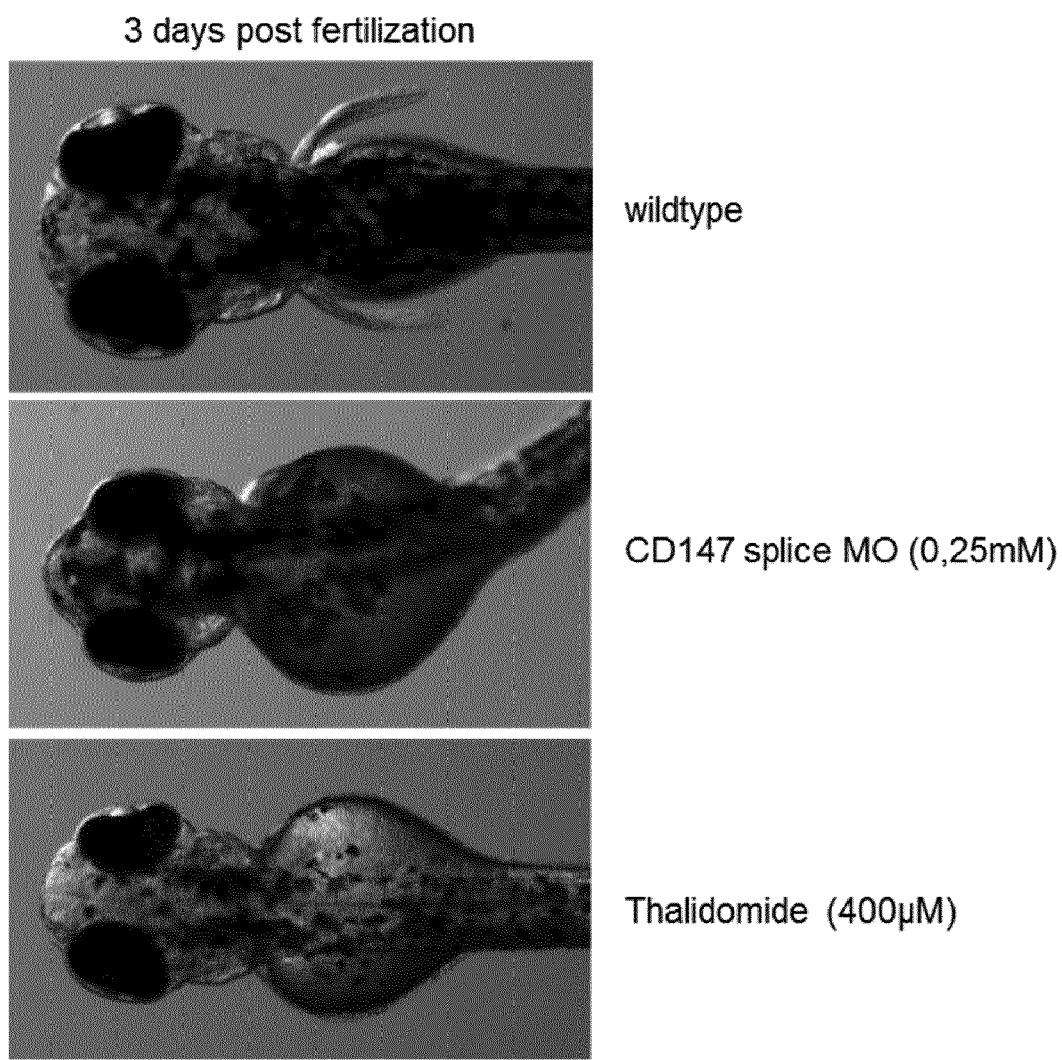

FIG. 11 shows that the knockdown of CD147 leads to a comparable teratotoxic phenotype as thalidomide.

On the day of fertilization zebrafish larvae were injected with 0.25 mM CD147 morpholino (splice MO), which prevent mRNA splicing and thus the expression of CD147, or treated with 400 μM thalidomide. On day 3 after fertilization zebrafish treated with CD147 morpholino or with thalidomide showed a similar phenotype with multiple malformations, inter alia, a smaller head, smaller eyes, shorter tight-fitting fins, and abdominal distension compared to the wild type.

Figure 12:
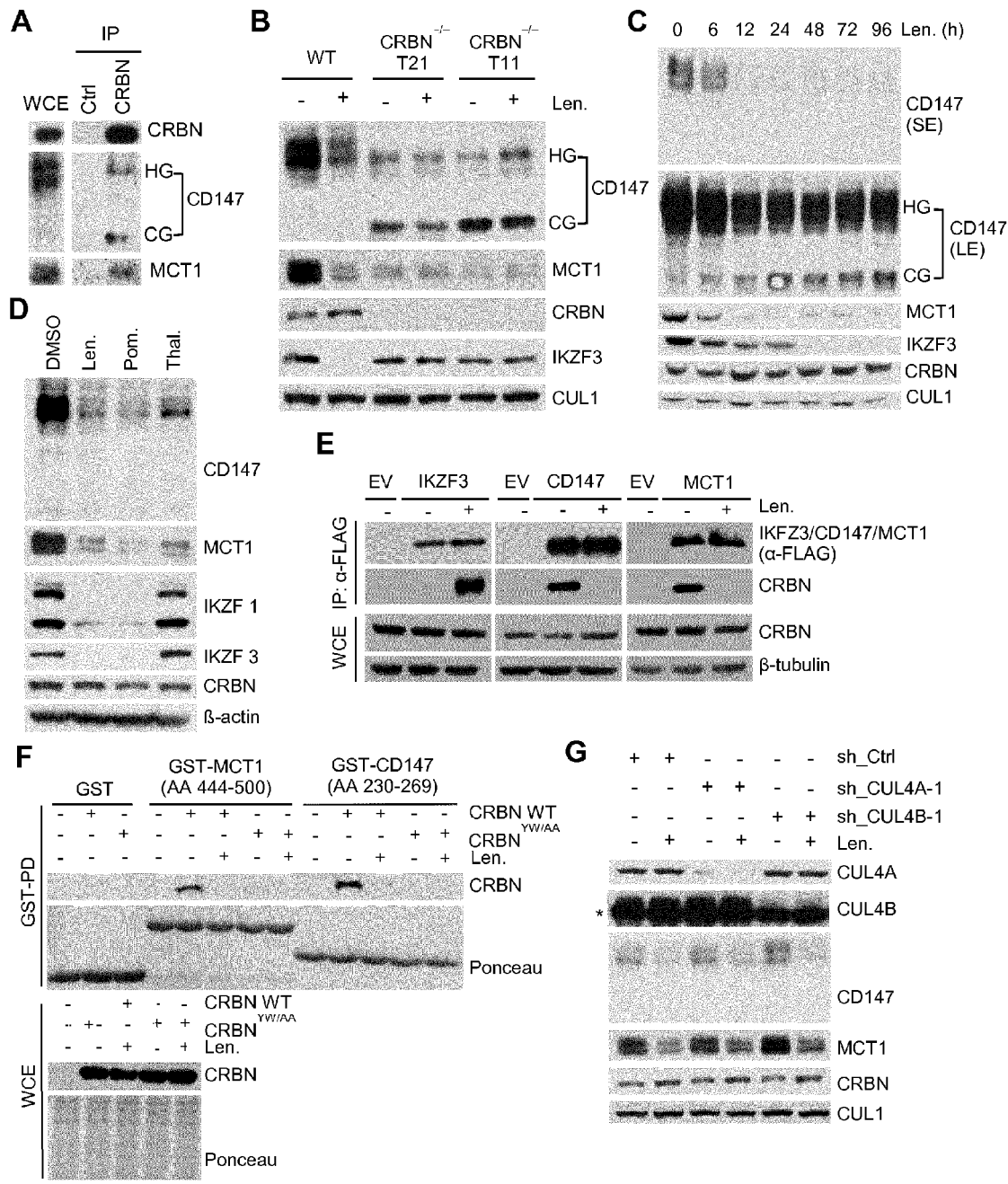

FIG. 12 shows that IMiDs compete with CRBN to destabilize CD147 and MCT1 in a ubiquitin-independent manner.

(A): Co-immunoprecipitation of endogenous CRBN, CD147, and MCT1 proteins from MM1S cells. CG, core-glycosylated; HG, high-glycosylated.

(B): Immunoblot analysis of parental (WT), and two $CRBN^{-/-}$ (T11, T21) MM1S myeloma lines. Cells were treated with 10 μM lenalidomide (Len.) for 96 hours as indicated.

(C): Immunoblot analysis of MM1S cells treated with 10 μM lenalidomide for the indicated times. SE, short exposure; LE, long exposure.

(D): Immunoblot analysis of MM1S cells treated with 10 μM lenalidomide, 100 nM pomalidomide (Pom.), or 100 μM thalidomide (Thal.).

(E): Immunoprecipitation of FLAG-tagged IKFZ3, CD147, and MCT1 in HEK293T cells treated with lenalidomide as indicated, and analysis of co-purified endogenous CRBN. DSS was used for protein crosslinking.

(F): Pull-downs of the indicated GST-tagged fragments of CD147 and MCT1 in whole cell extracts (WCE) of $CRBN^{-/-}$ HEK293FT cells reconstituted with either CRBN WT or a CRBN mutant harboring the mutations Tyr384Ala and Trp386Ala ($CRBN^{YW/AA}$). Precipitates were subjected to immunoblot analysis using the specified antibodies.

(G): Immunoblot analysis of MM1S cells in which expression of CUL4A and CUL4B was silenced by lentiviral transduction with the indicated shRNA constructs. Cells were treated with 10 μM lenalidomide (Len.) for 96 hours as indicated. The asterisk denotes an unspecific band.

Figure 13:
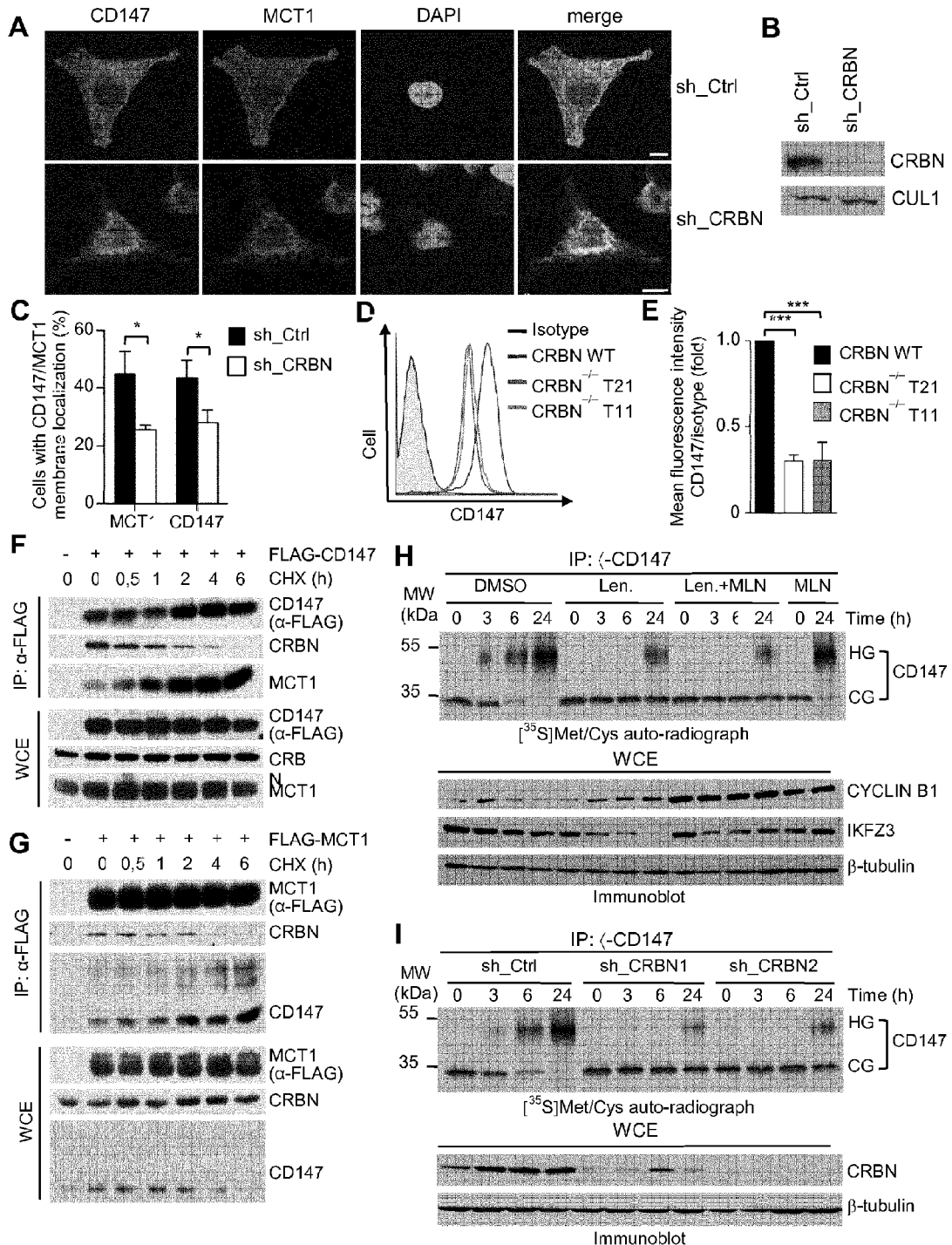

FIG. 13 shows that CRBN promotes maturation of CD147 and MCT1 proteins to mediate assembly and membrane localization of the CD147/MCT1 complex.

(A): Visualization of HeLa cells that were infected with the indicated shRNA constructs and transfected with expression constructs encoding HA-CD147 and FLAG-MCT1, followed by fixation with methanol and incubation with antibodies to HA (green) and FLAG (red). DNA was stained with DAPI (blue). Scale bars denote 10 μm.

(B): Immunoblot analysis of cells shown in (A) using the indicated antibodies.

(C): Quantification of cells shown in (a) with CD147/MCT1 membrane localization (n=3, mean±SD). *, P<0.05; Student's t test.

(D): Cell surface expression of endogenous CD147 in parental (WT; far right histogram), and two $CRBN^{-/-}$ MM1S myeloma lines (T11, T21) using flow cytometric analysis.

(E): Quantification of CD147 mean fluorescence intensities shown in (d) presented as CD147/isotype ratios (n=3, mean±SD). ***, P<0.001; one sample t test.

(F): FLAG-CD147 was immunoprecipitated (IP) from whole cell extracts (WCE) of HEK293T cells, and bound protein fractions were analyzed by immunoblotting. Cells were treated with cycloheximide (CHX) for the indicated times before lysis.

(G): FLAG-MCT1 was immunoprecipitated from HEK293T cells treated as in (f) and processed for immunoblot analysis.

(H): Autoradiographic analysis (upper panel) of CD147 immunoprecipitates from MM1S cells that were pulsed with □$^{35}$S□Met/Cys, treated with lenalidomide and/or MLN4924 as indicated, and chased for the specified times. Immunoblot analysis of the respective whole cell lysates (WCE) was performed with antibodies to the indicated proteins (lower panel). CG, core glycosylated; HG, high glycosylated (mature form).

(I): Autoradiographic analysis (upper panel) of CD147 immunoprecipitates from MM1S cells in which expression of CRBN was silenced by lentiviral transduction with the indicated shRNA constructs and which were pulsed and chased as in (h). Whole cell lysates were analyzed by immunoblotting (lower panel).

Figure 14:
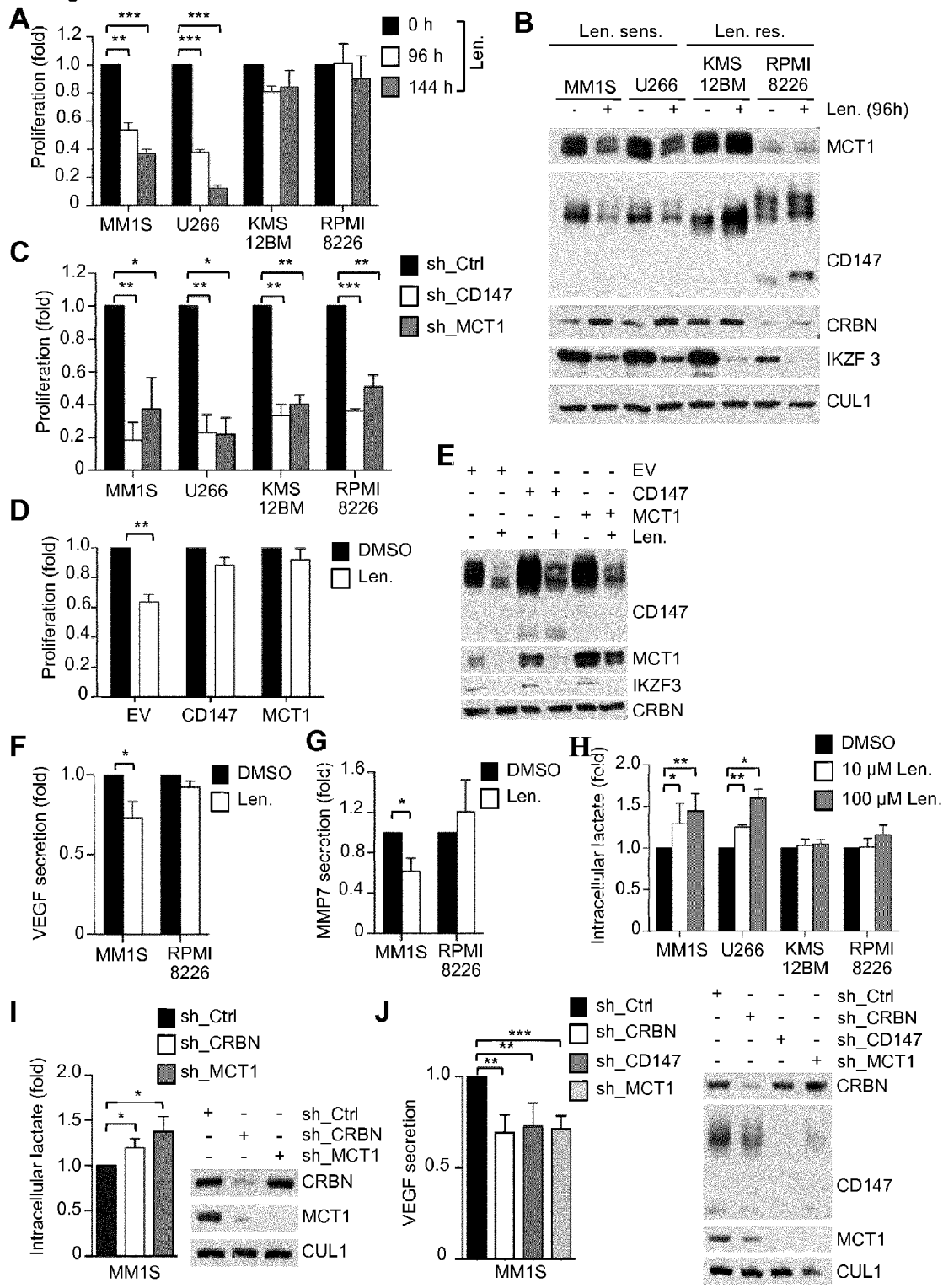

FIG. 14 shows that lenalidomide mediates anti-myeloma activity via CD147 and MCT1 destabilization.

(A): Cell proliferation of lenalidomide sensitive (MM1S, U266) and resistant (KMS12BM, RPMI8226) MM cell lines treated with lenalidomide (10 µM) for the indicated times (n=3, mean±SD). , P<0.01; *, P<0.001; one sample t-test.

(B): Representative immunoblot analysis of cells shown in (a) using antibodies to the indicated proteins. Quantification of the CD147 and MCT1 protein expression levels are shown in FIG. 22a.

(C): Cell proliferation analysis of the indicated MM cell lines in which CD147 and MCT1 were silenced by the specified shRNAs (n=3, mean±SD). *, P<0.05; , P<0.01; *, P<0.001; one-sample t-test. Respective immunoblot analyses are presented in FIG. 22b.

(D): Cell proliferation of MM1S cells that were infected with the indicated constructs to induce forced expression of CD147 and MCT1. Cells were then treated with 10 µM lenalidomide for 72 hours as specified (upper panel) (n=3, mean±SD). **, P<0.01; one-sample t-test. (E): Representative immunoblot analysis of cells shown in (d) using antibodies to the indicated proteins.

(F): Analysis of VEGF secretion in supernatants of the indicated MM cell lines treated with lenalidomide (10 µM, 96 h) as specified (n=3, mean±SD). *, P<0.05; one-sample t-test.

(G): Analysis of MMP7 secretion in MM cells treated as in (f) (n=3, mean±SD). *, P<0.05; one-sample t-test.

(H): Analysis of intracellular lactate levels in the indicated MM cells treated with lenalidomide as specified (MM1S, RPMI8226: n=5; U266, KMS12BM: n=3; mean±SD). *, P<0.05; **, P<0.01; one-sample t-test. (I): Analysis of intracellular lactate levels in MM1S cells in which CRBN and MCT1 were silenced by the specified shRNAs (left panel). CRBN and MCT1 expression was analyzed by immunoblotting (right panel) (n=4, mean±SD). *, P<0.05; one-sample t-test.

(J): Analysis of VEGF secretion in MM1S cells in which CRBN, CD147 and MCT1 were silenced by the specified shRNAs (left panel). CRBN, CD147 and MCT1 expression was analyzed by immunoblotting (right panel) (n=5, mean±SD). , P<0.01; *, P<0.001; one-sample t-test.

Figure 15:
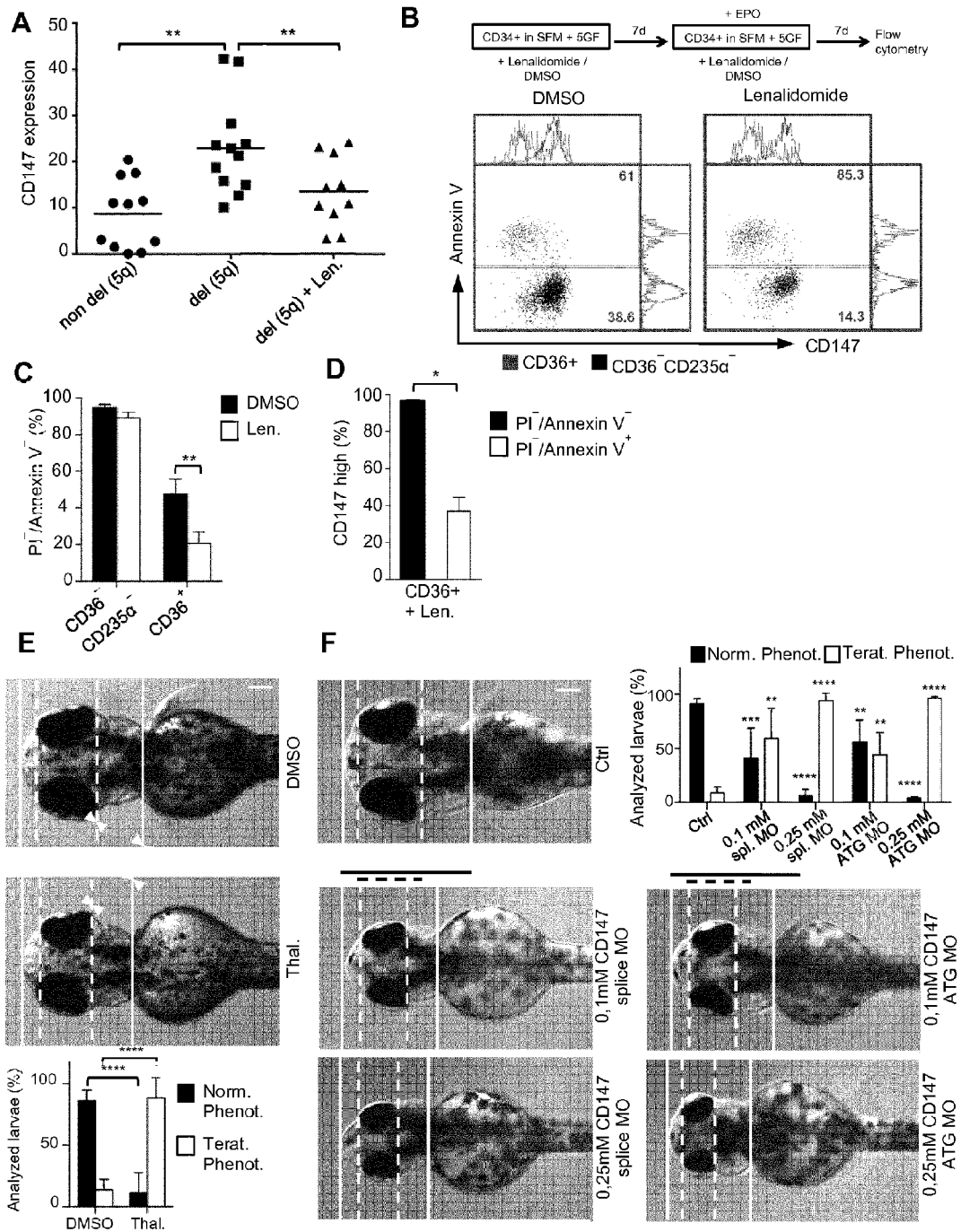

FIG. 15 shows the role of CD147 in human (del5q) MDS and IMiD-induced teratogenicity.

(A): Expression of CD147 on $CD45^{low}/CD235\alpha^+$ erythropoiesis in MDS bone marrow determined by flow cytometry. Data are shown as median fluorescence intensity relative to matched isotype control. Values for individual bone marrow samples from MDS patients with non-del(5q) (circles), untreated del(5q) (squares) and del(5q) on lenalidomide treatment (triangles) are shown. **, P<0.01; one-way ANOVA.

(B): Representative multiparametric flow cytometric analysis of del(5q) MDS bone marrow derived CD34+ cells that were propagated in vitro, stimulated towards erythroid differentiation, and treated with DMSO or lenalidomide as indicated. Overlay of dot plots from the non-erythroid (CD36−/CD235α−) and early erythroid (CD36+) compartments are shown to demonstrate apoptosis (Annexin V) in relation to CD147 expression. SFM: serum free medium; 5GF: 5 growth factors comprising kit ligand, FLT3-Ligand, TPO, IL3, and IL6; EPO: erythropoietin.

(C): Quantification of lenalidomide induced apoptosis in the non-erythroid (CD36−/CD235α−) and early erythroid (CD36+) compartments of cells shown in (b) averaged with two further independent samples (n=3, mean±SD). **, P<0.01; Student's t test.

(D): Quantification of CD147 expression in viable (PI−/Annexin V−) and apoptotic (PI−/Annexin V+) cells shown in (b) averaged with two further independent samples that were treated with lenalidomide (n=3, mean±SD). *, P<0.05; Student's t test.

(E): Zebrafish larvae at 3 dpf (days post fertilization), treated with either DMSO or thalidomide (upper two panels); anterior to the left, dorsal view. In contrast to DMSO treated larvae, thalidomide treated zebrafish display a teratotoxic phenotype including smaller eyes (dotted line) and smaller heads (solid line), and smaller fins. Scale bar represents 100 µm. Quantifications of larvae with reduced eye sizes as readout for a teratotoxic phenotype are shown in the lower panel (n=9, mean±SD). ****, P<0.0001; Student's t test.

(F): Zebrafish larvae at 3 dpf, treated with two different morpholinos (splice MO, ATG MO) at different concentrations versus control. Knock-down of CD147 results in identical phenotypes as thalidomide treatment shown in (e). Scale bar represents 100 µm. Quantifications of larvae with reduced eye sizes as readout for a teratotoxic phenotype are shown in the upper right panel (n=3 for CD147 splice MO at 0.1 mM, n=3 for CD147 splice MO at 0.25 mM, n=3 for CD147 ATG MO at 0.1 mM, n=4 for CD147 ATG MO at 0.25 mM; 50 eggs were injected and analyzed per individual experiment; mean±SD). , P<0.01; *, P<0.001; ****, P<0.0001; one-way ANOVA. Significance levels refer to the control samples.

Figure 16:
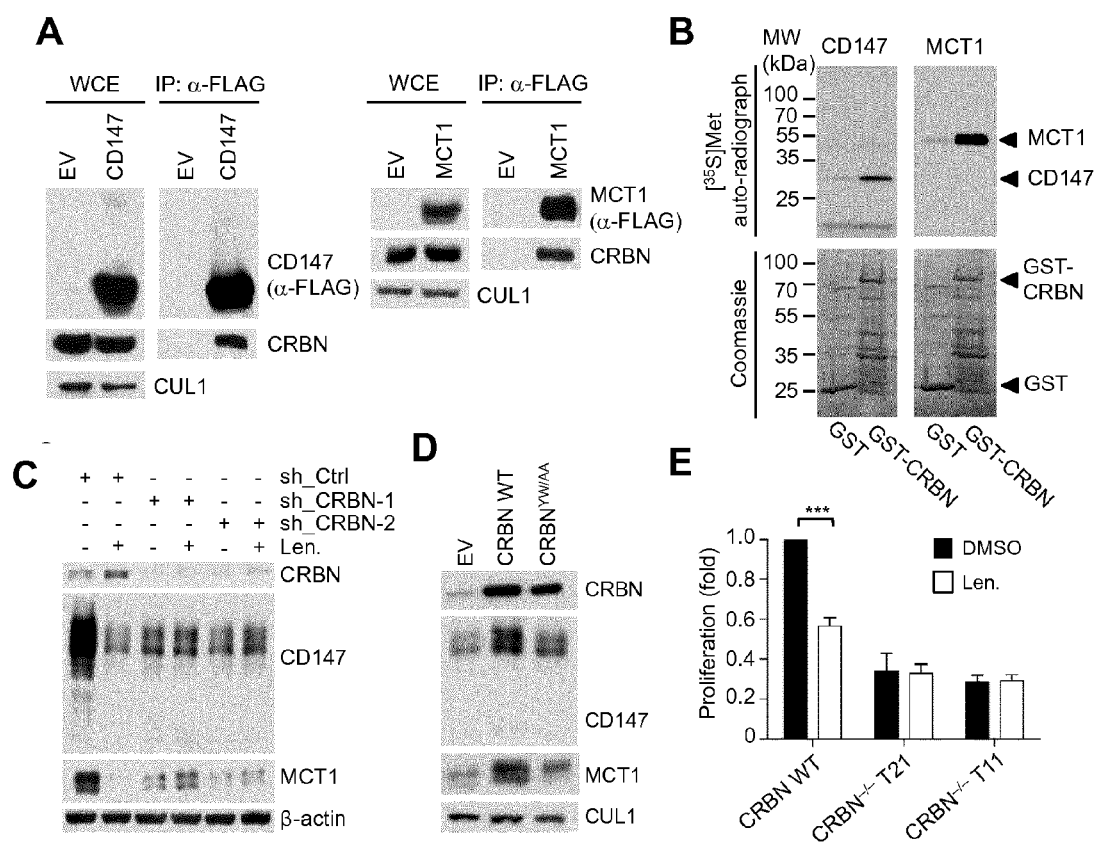

FIG. 16 shows that CRBN interacts with CD147 and MCT1 proteins to promote their stability and mediates MM cell proliferation.

(A): Immunoprecipitation of FLAG-CD147 (left panel) and FLAG-MCT1 (right panel) from HEK293T cells. Immunoprecipitates were analyzed by immunoblotting.

(B): Pull down assays of recombinant GST-CRBN and in-vitro translated and $^{35}$S-labeled CD147 and MCT1 proteins. Bound protein fractions were visualized by autoradiography.

(C): Immunoblot analysis of MM1S cells in which CRBN expression was silenced by lentiviral transduction with two independent shRNAs against CRBN (sh_CRBN). Cells were treated with 10 µM lenalidomide (Len.) for 96 hours as indicated.

(D): Immunoblot analysis of MM1S cells in which expression of CRBN WT or $CRBN^{YW/AA}$ was induced by infection with respective lentiviral expression constructs.

(E): Cell proliferation analysis of parental (WT), and two $CRBN^{-/-}$ (T11, T21) MM1S myeloma lines. Cells were treated with 10 µM lenalidomide (Len.) for 96 hours as indicated (n=3, mean±SD). ***, P<0.001; one-sample t-test.

Figure 17:
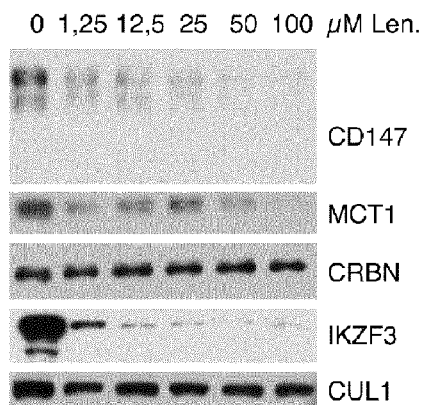

FIG. 17 shows that lenalidomide destabilizes CD147 and MCT1 in a dose dependent manner.

Immunoblot analysis using the indicated antibodies of MM1S cells treated with lenalidomide (Len.) at different concentrations for 72 hours.

Figure 18:
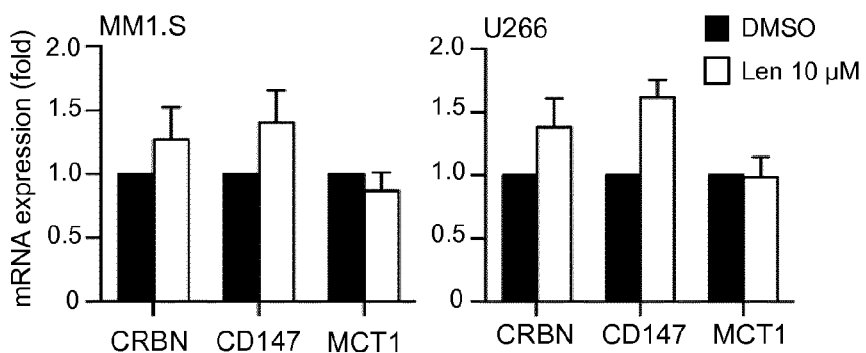
Figure 18:
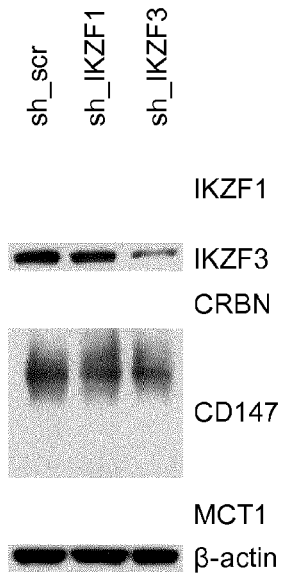

FIG. 18 shows that IMiD induced loss of CD147 and MCT1 expression is not regulated at the level of transcription.

(A): Real-time qPCR analysis of MM1S and U266 cell lines treated with 10 µM lenalidomide or vehicle as specified. The amount of mRNA in the vehicle (DMSO) treated sample of each gene was set as 1. (n=3, mean±SD)

(B): Immunoblot analysis of MM1S cells using the antibodies specified in which IKZF1 and IKZF3 expression was silenced by lentiviral transduction with the indicated shRNA constructs.

Figure 19:
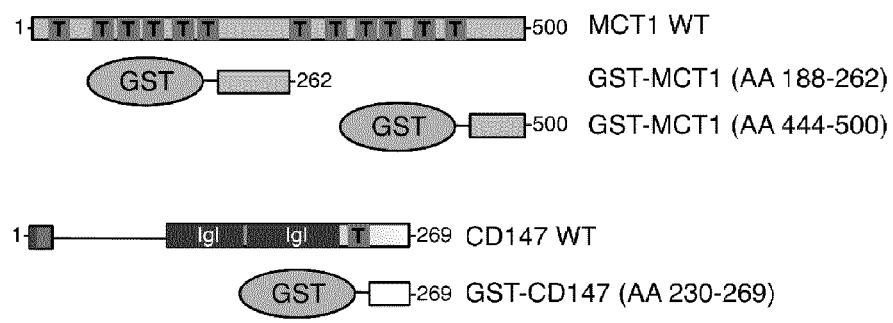
Figure 19:
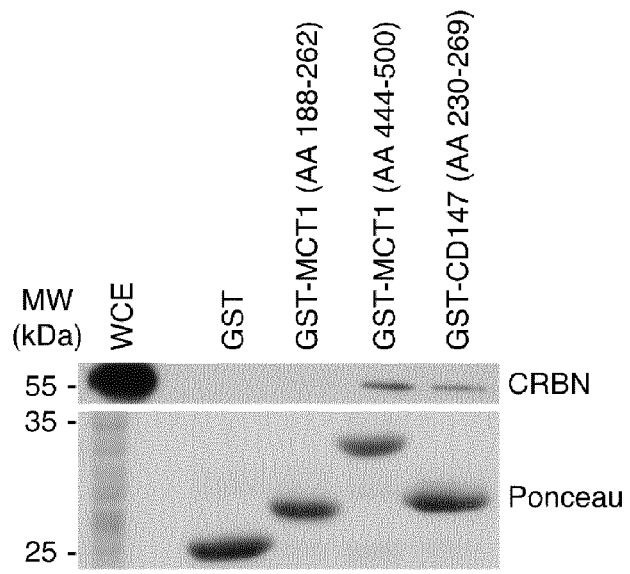

FIG. 19 shows that CD147 and MCT1 interact with CRBN via their C-terminal intracellular domains.

(A): Schematic of full-length human CD147 and MCT1 proteins and GST-tagged fragments of their intracellular domains. T, transmembrane domain, Igl, immunoglobulin-like domain.

(B): GST pull-downs of the indicated fragments of CD147 and MCT1 in whole cell extracts (WCE) of MM1S cells. Precipitates were subjected to immunoblot analyses and ponceau staining.

Figure 20:
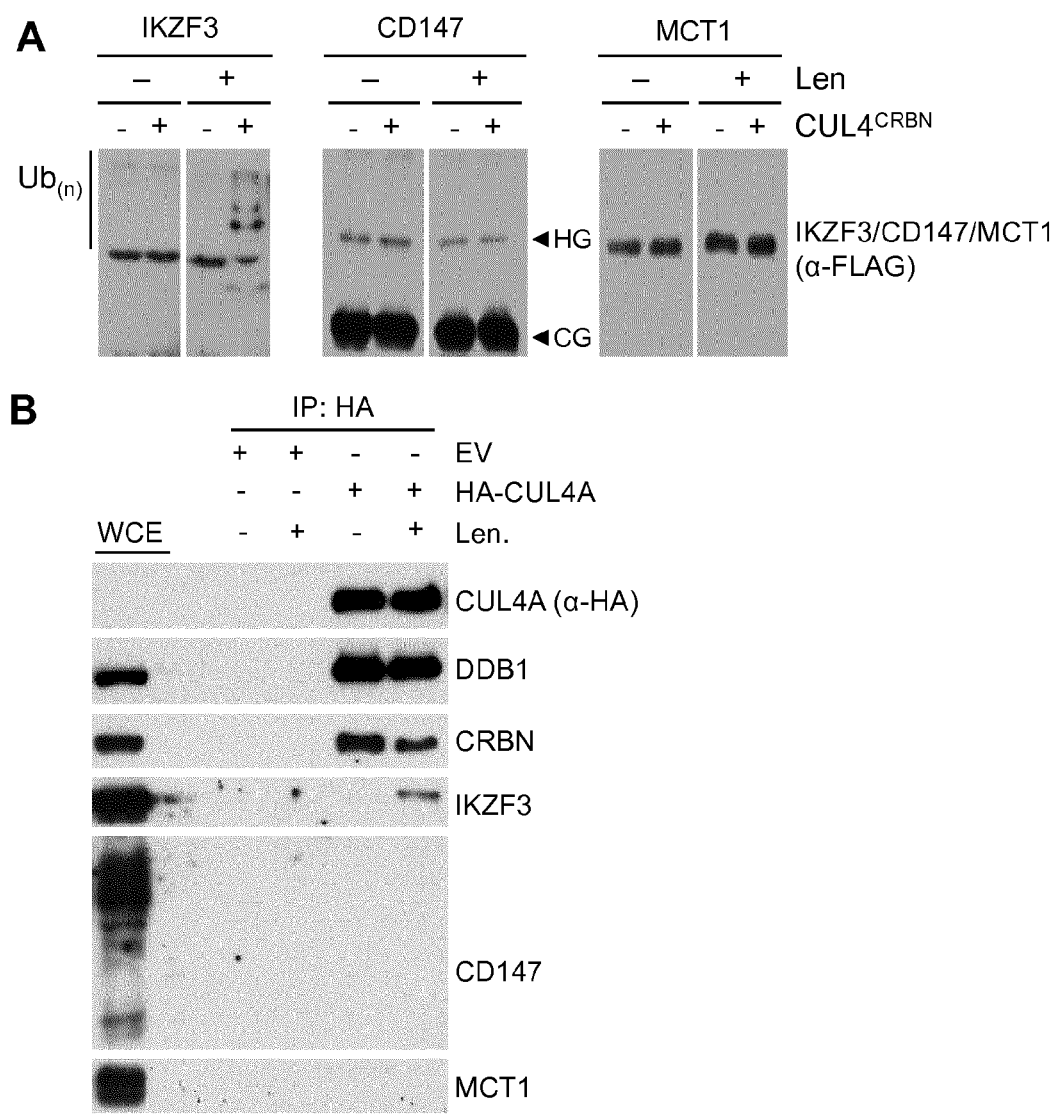

FIG. 20 shows that CRBN exerts its activity on CD147 and MCT1 in a ubiquitin-independent manner.

(A): The Cul4$^{CRBN}$ ligase complex does not ubiquitylate CD147 and MCT1 in vitro. In vitro reconstituted ubiquitylation assays of the indicated FLAG-tagged proteins conducted in the presence of the purified CRL4$^{cRBN}$ complex and E1/E2 enzymes as indicated. Components of the CRL4$^{cRBN}$ ligase complex (Cul4A, DDB1, ROC1, CRBN) were purified from baculovirus transduced insect cells, while FLAG-tagged substrates were derived from HEK293T cells. CG, core glycosylated; HG, high glycosylated; Ub(n), polyubiquitylated species.

(B): CD147 and MCT1 proteins do not associate with CUL4A. HA-CUL4A was purified from HEK293T cells and incubated with MM1S cell extracts that were treated with lenalidomide as specified. Bound protein fractions were subjected to immunoblot analysis using the indicated antibodies.

Figure 21:
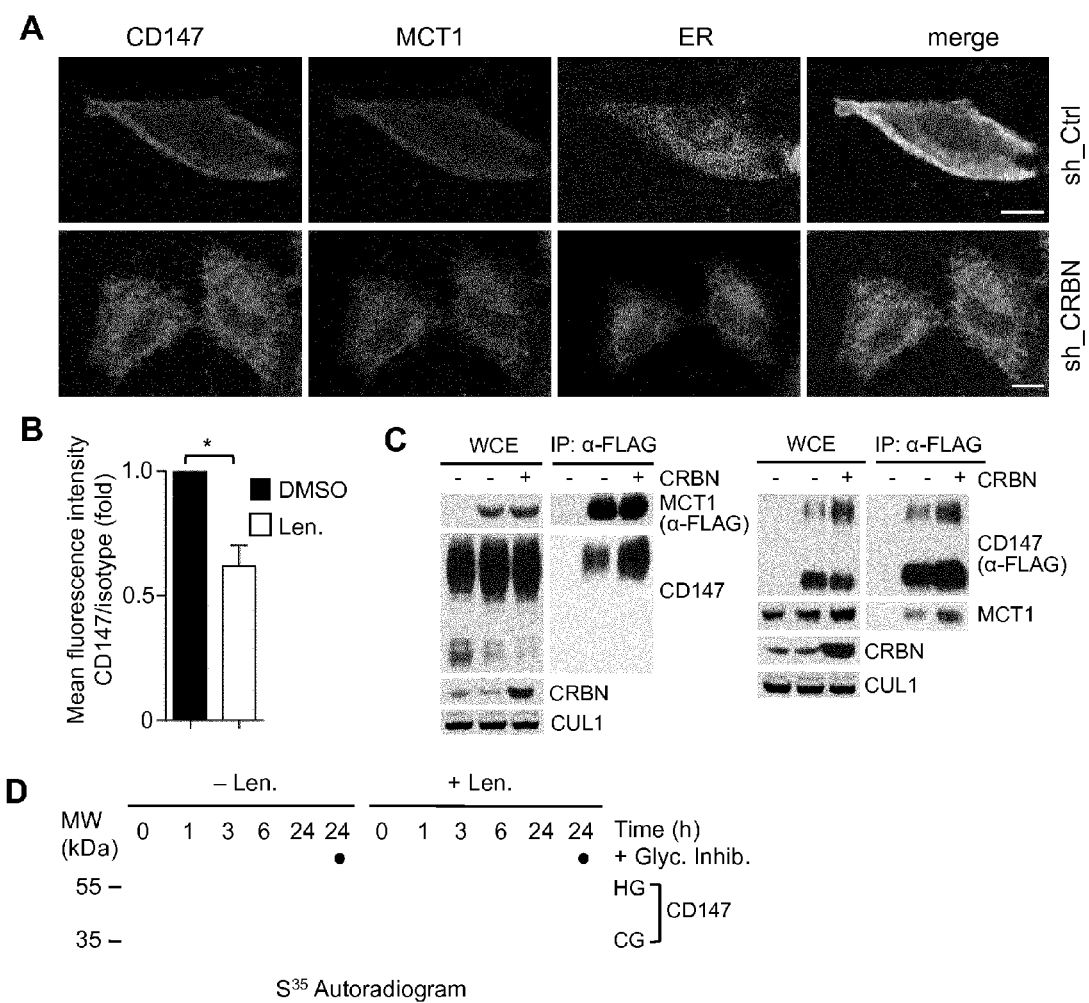

FIG. 21 shows that CRBN mediated maturation and membrane localization of the CD147/MCT1 complex is abrogated by lenalidomide.

(A): Silencing of CRBN results in accumulation of CD147 and MCT1 at the endoplasmatic reticulum. Visualization of HeLa cells stably expressing the indicated shRNA constructs and transfected with expression constructs encoding HA-CD147 and FLAG-MCT1. Cells were incubated with an ER-tracker (blue, third column) followed by fixation with paraformaldehyde and incubation with antibody to HA (green, first column) and FLAG (red, second column). ER, endoplasmatic reticulum. Scale bars represent 10 µM.

(B): Cell surface expression of endogenous CD147 in MM1S cells treated with lenalidomide (10 µM) as specified using flow cytometric analysis. Quantification of CD147 mean fluorescence intensities are shown presented as CD147/isotype ratios (n=3, mean±SD). *, P<0.05; one sample t test.

(C): Co-immunoprecipitation of FLAG-MCT1 with endogenous CD147 (left panel) or FLAG-CD147 with endogenous MCT1 (right panel) from HEK293T cells in which CRBN expression was induced by expression from a CRBN expression construct. Immunocomplexes were probed with antibodies to the indicated proteins.

(D): Autoradiographic analysis of CD147 immunoprecipitates from MM1S cells that were pulsed with $^{35}$S Met/Cys, treated with lenalidomide and/or the glycosylation inihibitor Tunicamycin as indicated, and chased for the specified times. CG, core glycosylated; HG, high glycosylated (mature form).

Figure 22:
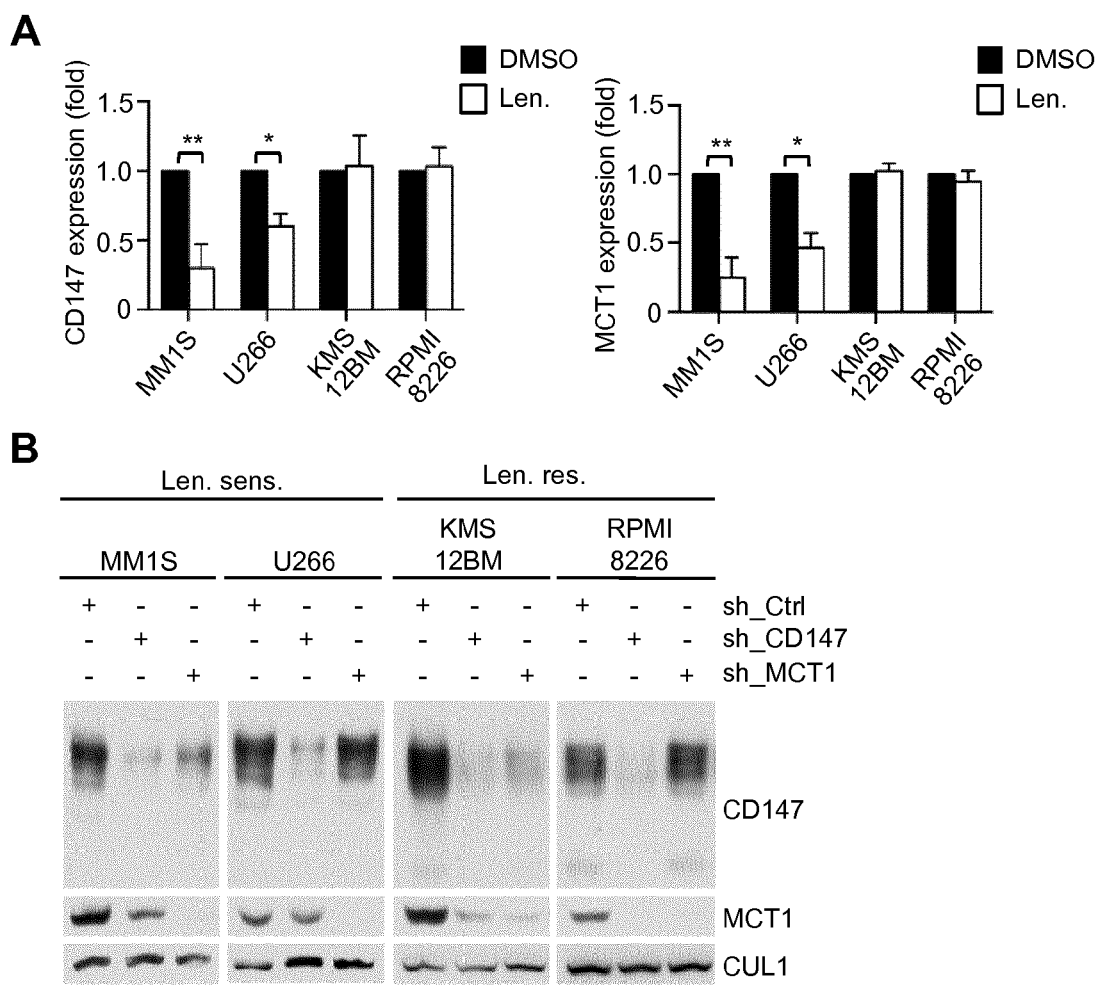

FIG. 22 shows that lenalidomide treatment and silencing of CD147 and MCT1 expression in different lenalidomide-sensitive and -resistant MM cell lines.

(A): Quantification of the CD147 and MCT1 protein expression levels of immunoblots shown in FIG. 14b averaged with two additional independent experiments (n=3, ±SD). *, P<0.05; , P<0.01; *, P<0.001; one sample t test.

(B): Immunoblot analysis of the indicated lenalidomide-sensitive and -resistant MM cell lines, in which CD147 and MCT1 were silenced by the specified shRNAs. The corresponding proliferation analysis is presented in FIG. 14d.

Figure 23:
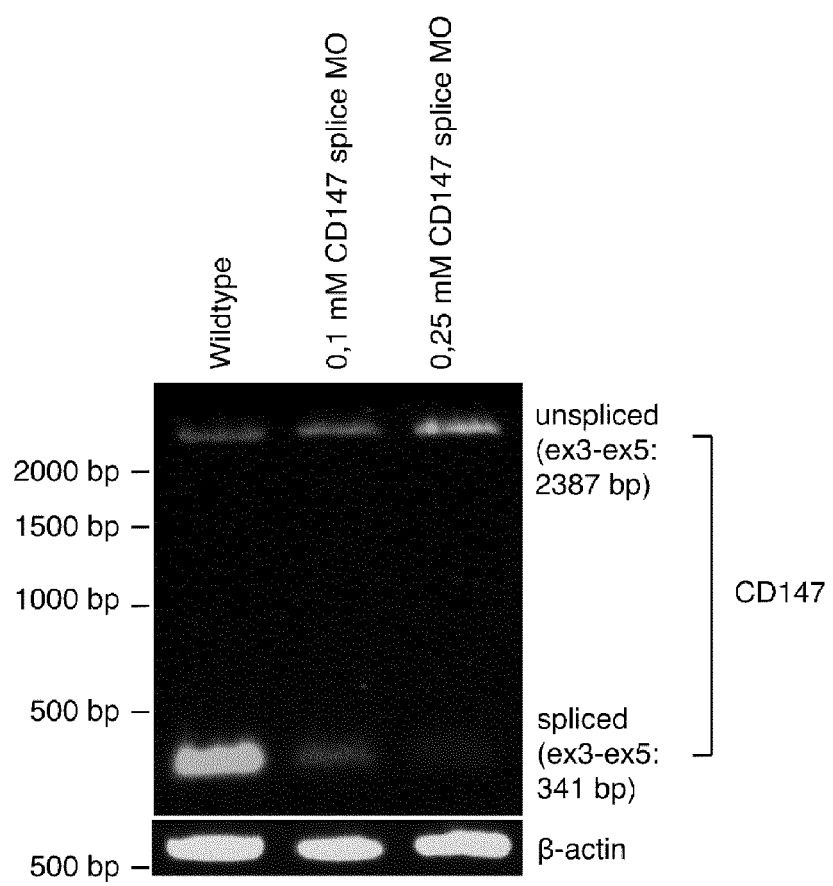

FIG. 23 shows the verification of efficient and dose dependent CD147 knockdown in CD147 morpholino treated zebrafish. Semiquantitative RT-PCR on cDNA extracted from zebrafish injected with CD147 splice morpholino (targeting the border of exon3/intron3) at the indicated concentrations or control. PCR was performed with CD147 fw primer in exon 3 and CD147 rv primer in exon 5, or β-actin primers as control.

DESCRIPTION OF THE PRESENT INVENTION

It was one problem to be solved by the present invention to provide a compound or a combination of compounds for use in treating diseases or conditions, which are sensitive to IMiD treatment, such as hematological and non-hematological malignancies. It was a further problem to provide a method of rapidly identifying IMiD resistant patients and to provide an alternative treatment regimen for treatment of the IMiD resistant patients. The inventors now identified novel substrates and interactors of CRBN, which can be used as biomarkers and/or additional therapeutic target structures for the improvement of therapeutic options for treating malignancies or premalignant conditions, in particular hematological and non-hematological malignancies. Furthermore, with the method provided by the inventors, IMiD resistant patients can be rapidly identified prior to extensive IMiD treatment, thereby avoiding ineffective treatment and the accompanying severe side effects of IMiD treatment. With the method of the present invention, patients who develop an IMiD resistance during treatment can be identified as well.

Figure 1:
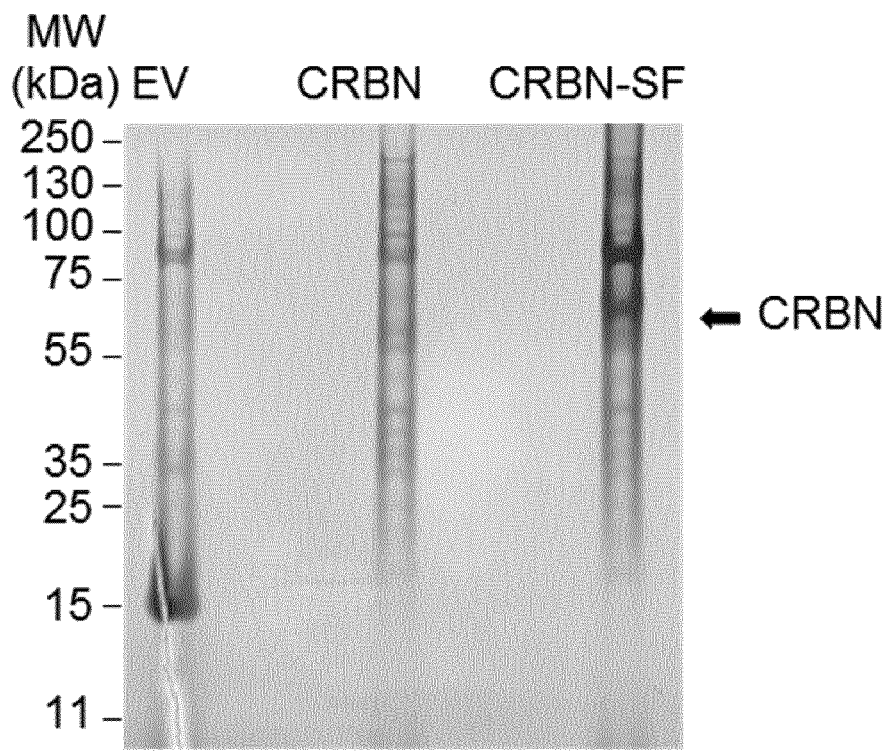
FIG. 1 shows the identification of CD147 and MCT1 as interactors of CRBN via tandem affinity purification of CRBN followed by mass spectrometry analysis.

The novel physiological substrates of CRBN were identified by tandem affinity purification. In contrast to methods that were used to identify IZKF1 and IZKF3 as IMiD induced substrates [1, 2], tandem affinity purification is an approach to detect physiological substrates. The ubiquitin ligase CRBN was labelled with two different tags (Strep-flag), overexpressed in HEK 293T cells, and then subjected to tandem affinity protein purification. After purification and elution, the resulting isolated protein pellet, which contained CRBN itself and its physiological interactors bound to it, was analyzed by mass spectrometry (see FIG. 1A). In this way, two membrane proteins, CD147 and MCT1, were identified as specific interactors of Cereblon (CRBN) (see FIG. 1B). Specifically, eight unique peptides corresponding to CD147 and six unique peptides corresponding to MCT1 were identified in the screen. Specificity of this interaction was ascertained via bidirectional co-immunoprecipitation studies and a complementary in-vitro approach using recombinant proteins, suggesting direct interaction (see FIGS. 1, 2, and 12A; FIG. 16 A,B).

CD147, which is also called Basigin or EMMPRIN (Extracellular matrix metalloproteinase inducer), is a multiple glycosylated membrane protein, which is inter alia involved in the induction of matrix metalloproteinases (MMPs). The secretion of MMPs promotes the invasiveness of tumor cells and is also important for angiogenesis. The latter is additionally stimulated via CD147-mediated secretion of vascular endothelial growth factor (VEGF). VEGF also seems to promote the migration and proliferation of myeloma cells. CD147 itself also plays an important role in multiple myeloma. It is overexpressed in myeloma cells, and the level of CD147 expression correlates with the rate of proliferation of myeloma cells, whereas a knockdown of CD147 inhibits their growth. In other tumor entities such as hepatocellular carcinoma or prostate cancer, the expression of CD147 correlates with invasiveness and metastasis. As these are also the entities that had previously been shown to be IMiD sensitive, a connection between CD147 expression and sensitivity to IMiD seems to be present.

In addition to these functions CD147 is known to bind as a kind of chaperone molecule to MCT1 (monocarboxylate transporter 1), a protein which was also identified as a physiological substrate of CRBN by the inventors of the present invention.

The ubiquitously expressed MCT1 is a H+/lactate symporter, which needs binding to CD147 for its regular expression and membrane localization. MCT1 is involved in the transmembrane lactate transport, which is used in aerobic (tumor) cells to import lactate for oxidative metabolism. In anaerobic tumor cells, which derive their energy from anaerobic glycolysis, MCT1 is however involved in the export of lactate from the cell. As well as CD147, MCT1 is often overexpressed in tumor cells and is associated with increased invasiveness in several cancers. In multiple myeloma, MCT1 plays an important role for lactate export and cell proliferation as well.

It was demonstrated by co-immunoprecipitation methods that CRBN binds to both CD147 and MCT1 (see FIG. 2-4, FIG. 12A, FIG. 16 A,B). Further studies showed that in the presence of IMiDs the bond between CRBN and CD147/MCT1 is significantly weakened, as is the binding between CD147 and MCT1 itself (see FIG. 3-5, FIG. 12 E,F). Since CD147 and MCT1 stabilize each other, it is contemplated that an inhibition of the interaction between CD147 and MCT1 would lead to a destabilization of these proteins. It was indeed shown by the inventors, that under IMiD treatment of myeloma cells protein levels of both MCT1 and CD147 decreased, and lactate export was reduced (see FIG. 6, FIG. 9B, FIG. 10, FIG. 14B,H). Moreover, a lower rate of proliferation and increased apoptosis rate could be detected (see FIG. 9, FIG. 14A-C). IMiD resistant cell lines such as RPMI-8226 and KMS-12-BM did not exhibit these characteristic changes in the level of lactate export, cell proliferation and in the apoptosis rate (see FIG. 9, FIG. 14A,B, FIG. 14H). Surprisingly, both sh-mediated knockdown as well as CRISPR/CAS mediated knockout of CRBN in myeloma cells led to the same effects of reduction of CD147 and clear decrease in MCT1 expression (see FIG. 7C, FIG. 8A, FIG. 12B). Knockdown/knockout of CRBN also led to decreased membrane localization of CD147 and MCT1, as shown by immunofluorescence nad flow cytometry (see FIG. 8, FIG. 13A-E).

By further studies it was also demonstrated that CRBN mediates maturation and stabilization of the CD147/MCT1 complex in an ubiquitin-independent manner (see FIG. 12B,C,G, FIG. 13F-I, FIG. 20A,B), and that IMiDs compete with CD147 and MCT1 for CRBN binding to exert versatile anti-tumor and teratogenic effects. These findings provide different novel aspects of CRBN function and IMiD biology.

First, an ubiquitin-independent function for CRBN is disclosed. Ubiquitin ligase activity is not intrinsic to CRBN, but instead requires the integration of CRBN into the multi-subunit CRL4 ubiquitin ligase. The data presented in this application suggests a dual activity of CRBN that comprises a ubiquitin-dependent function within the CRL4 ligase complex, and a ubiquitin- and CRL4-independent chaperone-like function. Such a dual function solves the currently existing paradox with regard to the well-documented synergistic anti-myeloma activity of IMiDs and proteasomal inhibitors as bortezomib, carfilzomib, and ixazomib, as proteasomal inhibition would be expected to antagonize the effect of IMiDs on IKZF1/3.

Second, the identification of CD147 and MCT1 as specific interactors or "client proteins" of CRBN provides a functional explanation for various anti-tumor effects of IMiDs, including anti-angiogenesis and anti-invasion, and adds metabolic targeting as a new mode of action of IMiDs. In fact, both MM and MDS are malignancies of the bone marrow, which is characterized by an environment of local hypoxia and the need for anaerobic glycolysis for energy production, thereby making lactate export essential. Importantly, it is also shown that all three established IMiDs (thalidomide, lenalidomide, pomalidomide) destabilize CD147/MCT1, indicating a general drug-class specific effect, whereas IKZF1/3 degradation appears to be restricted to lenalidomide and pomalidomide.

Third, given the broad expression of the CD147/MCT1 complex in early stages of development and overexpression in various malignancies, a common mechanism for IMiD-mediated teratogenicity and IMiD induced anti-tumor activity in the lymphoid context and beyond is provided.

Finally, the surface localization of the CD147/MCT1 complex as well as its importance for proliferation and survival, distinguishes CD147/MCT1 as a well accessible therapeutic target structure in IMiD responsive and resistant tumors In summary, it is thus contemplated that CRBN exerts a stabilizing effect on CD147 and MCT1, which is in turn inhibited by IMiDs. It is further contemplated, without being bound by this theory that the decreasing protein levels of MCT1 and CD147 can be explained by the elimination of the stabilizing effect of CRBN.

It was shown by the inventors that IMiD treatment leads to a destabilization of the protein levels of CD147 and MCT1 in IMiD-sensitive, but not IMiD-resistant myeloma cells. Thus, the protein levels of CD147 and MCT1 can be used to assess the efficacy of an IMiD treatment. The protein levels of CD147 and MCT1 are therefore biomarkers of IMiD treatment efficacy.

A biomarker, or biological marker, generally refers to a measurable indicator of some biological state or condition. For the purpose of the description of the present invention, the biomarker is used to indicate IMiD treatment efficacy. Prior and during IMiD treatment, the protein level of MCT1 and/or CD147 in a sample obtained from the patient is measured. Prior and after IMiD administration, samples can be obtained from the patient, and the protein levels can be measured and compared to an initial reference level or to any previously measured level to monitor efficacy of the IMiD treatment. The initial protein level prior to start of IMiD treatment can be used as a reference. If no initial protein level prior to start of IMiD treatment is available, for example because no sample has been obtained prior to the start of the IMiD treatment, the reference value for the protein level will have to be set to a standard value or baseline as will be known to the person of skill in the art.

Under efficacious IMiD treatment the initial level of MCT1 and/or CD147 will decrease significantly, as shown in FIGS. 6 and 9. When the IMiD treatment is not efficacious, the protein level will not decrease during IMiD treatment or will, after an initial decrease, increase to about the initial level as determined prior to the start of the IMiD treatment. If no initial protein level is available as a reference value, then an observed statistically significant increase of the protein level compared to the protein level in previously obtained samples over the course of treatment is indicative of IMiD resistance development. If a statistically significant increase compared to the statistically significant decreased protein level is observed, it is determined that the patient treated with IMiD is developing or has developed a resistance to IMiD over the course of the treatment. The usual interval between taking of samples and assessing of protein level can be concurrent with the dosage regimen. For example, prior to each new cycle of IMiD treatment, a sample is taken, followed by the next sample within a 2 week period. Samples can be obtained several times after an IMiD dosage administration. For example, a sample can be taken once every week, or once every 2 weeks, or once a month, following an IMiD dosage administration. If an increase of the protein level is observed, which is not significant, the protein levels have to be monitored very closely as the increase can nevertheless be indicative of the start of a IMiD resistance development. If this is the case, the interval between obtaining of samples can be shortened, to more closely monitor protein levels.

Decrease of the protein level is any decrease that is statistically significant. Preferably the decrease is to about at least 50%, 20%, or 10% of the initial level prior to start of the treatment regimen. Increase of the protein level is any increase that is statistically significant. Preferably the increase is from the about at least 50%, 20%, or 10% of the initial level prior to start of the treatment regimen to about at least 80%, or 90%, 100% of the initial level prior to start of the treatment regimen. A statistically significant increase of the protein level compared to a respective protein level in a sample obtained previously over the course of treatment can be at least 2-fold, 3-fold, 4-fold, 5-fold, or at least 10-fold. The statistic significance of the decrease or increase of the protein level can be determined by any useful statistical analysis method as known to the person of skill in the art. For example the statistical significance can be determined by determining the p-values using a Student's t-test or a chi-squared test.

The statistically significant decrease or increase of the protein level or the lack thereof can be observed in samples obtained from a patient treated with IMiD within a time period starting with the administration of a dosage of the IMiD, wherein the time period is less than 3 weeks, or less than 2 weeks, or less than 1 week. Preferably the samples are obtained from the patient less than 2 weeks after the administration of a dosage of the IMiD.

Therefore, by assessing and monitoring the protein level of MCT1 and/or CD147 within a short time period after start of an IMiD treatment, a physician can rapidly decide whether a patient responds or continues to respond favorably to the IMiD treatment and can determine the most effective dose of the medication to be administered, or, if an IMiD resistance is detected, the physician will know that he has to try a different treatment approach. Thereby unnecessary ineffective treatment, and the accompanying side effects are avoided, and no time and resources are wasted with the ineffective treatment.

Therefore, the present invention provides a method of assessing the efficacy of an IMiD treatment regimen by determining the protein level of CD147 and/or MCT1 in a sample obtained from the subject, comprising cancerous or premalignant cells.

In the method of the invention, MCT1 and/or CD147, which are physiological substrates of CRBN, are used as biomarkers, wherein a decrease in the protein level in a sample obtained from a subject during treatment with an IMiD is compared to the respective level in a sample obtained from the subject prior to the start of said treatment. A decrease of the CD147 and/or MCT1 protein level is expected to be seen within few days of treatment (e.g. after 1 week or less after beginning of IMiD treatment), and would therefore allow assessment of clinical response much earlier than other parameters used for evaluation for treatment response (e.g. plasma cell population in bone marrow).

The protein level can be measured by methods known to the person of skill in the art such as Western Blot and immunohistochemistry. As MCT1 and CD147 are proteins localized at the cell membrane, they are easily accessible for cell surface based diagnostic methods, such as flow cytometry. Therefore, evaluation of expression level of these proteins can be carried out efficiently.

Thus in one embodiment a method is provided, wherein in a first step, samples comprising the (pre)-malignant cells are obtained from the patient. For example, if the patient is suffering from multiple myeloma, the sample will comprise malignant plasma cells, and will be obtained by aspiration of bone marrow. The obtained bone marrow sample can then be analyzed for protein levels of CD147 and/or MCT1 by methods such as flow cytometry or immunohistochemistry. The bone marrow sample or isolated plasma cells can also be further processed for detection of the protein level of MCT1 and/or CD147 as is known to the person of skill in the art. Further methods for determining the concentration levels of these proteins such as western blot are known to the person of skill in the art.

In a further aspect of the invention, MCT1 and/or CD147 can be used as target structures for therapeutic strategies as it has been shown that these proteins are overexpressed in cancerous cells, such as malignant plasma cells. It has also been shown, that under efficacious IMiD treatment, the protein levels of MCT1 and CD147 decrease. Therefore, according to this aspect of the invention, inhibition of the biological function of MCT1 and/or CD147 will support and even enhance an IMiD treatment and, moreover, provide treatment alternatives to IMiDs particularly in IMiD resistant cases or entities. The present invention provides a combination of inhibition of the novel identified CRBN substrates CD147 and/or MCT1 with IMiD treatment that will lead to a reduction in the dosage needed for an effective IMiD treatment. This reduction of the dosage will also lead to a decrease in the risk of the patient developing an IMiD resistance.

The biological function can be inhibited on mRNA level, leading to less translated protein, or on protein level, leading to either degradation or blocking of the protein.

In any case, the inhibition will result in less or no protein capable of carrying out the biological functions, such as lactate transport or VEGF-secretion /MMP induction. This will lead to a decrease of the proliferation rate of the cancerous cells, and to an increase of the apoptosis rate. Therefore, inhibition of the biological function of MCT1 and/or CD147 during IMiD treatment will improve the currently used IMiD treatment regimens and provide also IMiD-independent treatment approaches for the treatment of IMiD resistant entities.

The inhibitor can be a molecule, a natural or synthetic nucleic acid or nucleic acid analog, antisense molecule, small interfering RNA (siRNA), protein, peptide, antibody, antigenic fragment, chemical compound or the like, which inhibits protein expression of CD147 or MCT1 on the transcriptional or translational level, binds CD147 or MCT1 and inhibits one or more biological activities of CD147 or MCT1. The terms "inhibit" or "inhibition" respectively comprise any change in protein expression, in biological activity or function of CD147 or MCT1 such as reduction or decrease of the activity or function such as interaction with CRBN or neutralizing of its activity or function.

The successful inhibition's effect on the biological activity of CD147 and/or MCT1, such as lactate export, or influence on apoptosis rate and/or proliferation rate, can be determined with a bioactivity assay as is known in the art. For example, and as shown in principle in FIGS. 9 and 10, the apoptosis rate and/or proliferation rate can be determined by survival assays or apoptosis assays, and/or the lactate transport function can be assayed by intracellular and extracellular lactate measurements.

Furthermore, if the inhibition occurs on mRNA level, its effect can be detected by measuring the protein level of the respective protein. A successful inhibition leads to a significant decrease of the protein level. Indicator for a successful inhibition can also be a decrease in protein at its native localization, namely the cellular membrane. The proteins need to be localized at the cellular membrane to carry out their biological functions. Therefore, functional, biologically active MCT1 and CD147 are localized at the cellular membrane. Localization of the proteins can be shown by immunohistochemistry methods as shown in FIG. 8 or by immunofluorescence methods as shown in FIG. 6B.

The inhibition can occur directly on protein level by binding of an inhibitor to CD147 or MCT1 or indirectly by binding to a protein that needs to interact with CD147 or MCT1 to enable their respective biological functions such as CRBN. Specifically the inhibition of CD147 and/or MCT1 can be inhibition of the protein-protein interaction, or inhibition of the enzymatic activity, or an inhibition, which prevents the proteins from correctly localizing at the membrane. When the proteins are not trafficked to their native localization at the cellular membrane, they are retained and degraded in the endoplasmatic reticulum. Furthermore, the inhibition can occur by marking the proteins for proteasomal degradation.

The inhibition can also occur on mRNA level by destabilizing or degrading the mRNA. This can for example be achieved with therapeutic siRNA techniques. Small interference RNA targeting the mRNA of CD147 and/or MCT1 can be delivered to the cancerous cell and lead to a degradation of their respective mRNA. This leads to a decrease of translation into the respective proteins. Efficacious non-viral delivery systems, including direct chemical modification of siRNA, liposome formulations, nanoparticles, and targeting moieties have been developed to ensure that the siRNA molecules arrive at their intended target. This inhibition leads to less protein translated, and therefore to a decrease in the biological function of the protein.

Further examples for an inhibitor are molecules that bind to an epitope or active part of CD147 or MCT1, such as natural or synthetic nucleic acids or nucleic acid analogs, antisense molecules, small interfering RNAs (siRNA), proteins, peptides, antibodies or antibody fragments, ligands or conjugates and thereby reduces, decreases, neutralizes or prevents the biological activity of CD147 or MCT1.

In a preferred embodiment the inhibitor of the present invention is an antibody. The antibody can be polyclonal or monoclonal, and the term "antibody" is intended to encompass both polyclonal and monoclonal antibodies. The terms polyclonal and monoclonal refer to the degree of homogeneity of an antibody preparation, and are not intended to be limited to particular methods of production. The term "antibody" as used herein also encompasses chimeric, humanized, primatized, veneered or single chain antibodies, and functional fragments thereof. Functional fragments include antigen-binding fragments, which bind to a mammalian CD147 or MCT1. Such functional antibody fragments typically comprise antibody parts with a binding site corresponding to the antibody, composed of a light and a heavy chain, such as $F_v$-, $F_{ab}$- or $F(_{ab'})_2$-fragments or single-chain antibody fragments (scF$_v$). Shortened double strand fragments, such as $F_v$-, $F_{ab}$- or $F(_{ab'})_2$ are preferred. $F_{ab}$ and $F(_{ab'})_2$-fragments have no $F_c$-fragment, which would be present for instance in an intact antibody, therefore, they may be transported faster in the blood circulation and show comparably less non-specific tissue binding than intact antibodies. Moreover, because of the missing $F_c$ part they cannot elicit an undesired rejection. Such fragments can be produced by enzymatic cleavage or by recombinant techniques. For example, papain, pepsin or other protease with the requisite substrate specificity can also be used to generate fragments. Antibodies can also be produced in a variety of truncated forms using antibody genes in which one or more stop codons has been introduced upstream of the natural stop site. Methods to produce suitable antibodies are known to the person of skill in the art. Examples of anti-CD147 antibodies are known to the person of skill in the art [9]. Examples of MCT1 inhibiting compounds are known to the person of skill in the art as well.

Preferably, as CD147 and MCT1 are easily accessible being localized at the membrane of the cell, the inhibitor can be an antibody, which binds and inhibits one or more biological activities or functions of CD147 and/or MCT1. As CD147 and MCT1 need to be present in a complex to be stable, it is contemplated that by inhibition either CD147 or MCT1, the forming of the CD147/MCT1 complex is inhibited, which leads to a destabilization of both proteins. Without being bound by theory, it is therefore contemplated that by using one inhibitor, both proteins are inhibited.

The successful inhibition of MCT1 and/or CD147 provides the therapeutic effect as described above. This inhibition can be used as a therapeutic treatment in combination with an IMiD treatment. Therefore the present invention provides a combination of an IMiD and an inhibitor of MCT1 and/or an inhibitor of CD147 for use as a medicament.

In particular, the present invention provides a combination of an IMiD and an inhibitor of MCT1, and/or an inhibitor of CD147 for use in treating a disease in a subject, wherein the disease is a cancer or pre-malignant condition, which is associated with the overexpression of CD147 and/or MCT1 compared to the respective expression in healthy tissue. In particular the disease can be associated with the overexpression of both CD147 and MCT1 compared to the respective expression in healthy tissue.

The present invention also provides compounds for use in treating IMiD resistant patients. IMiD resistance can be determined as described above by using the method of assaying and comparing the protein level of MCT1 and/or CD147 in samples obtained from the patient. These patients will not or no longer benefit from an IMiD treatment due to the resistance. Due to resistance specificity, they will however still be susceptible to compounds which inhibit the interaction with CRBN in similar ways as the IMiD does or which inhibit MCT and/or CD147 directly. Such compounds are the inhibitors of MCT1 and/or CD147.

Therefore, the present invention also includes an inhibitor of CD147, and/or inhibitor of MCT1 for use in treating a disease associated with the overexpression of CD147 and/or MCT1 compared to the respective expression in healthy tissue in a subject, wherein the subject is IMiD resistant.

The disease to be treated can be any disease, preferably a cancer or pre-malignant condition, associated with overexpression of CD147 and/or MCT1 compared to the respective expression in healthy tissue. Therefore, the disease can be selected from any cancer, or pre-malignant condition, wherein CD147 and/or MCT1 are overexpressed. In particular, the cancer can be a solid cancer such as hepatocellular cancer, lung, gastric, breast, colorectal, or prostrate cancer, or it can be a hematological malignancy. The hematological malignancy can be acute myeloid leukemia (AML), myeloma, multiple myeloma, myelodysplastic syndrome (MDS), the del(5q) variant of the myelodysplastic syndrome (MDS), monoclonals gammopathy of undetermined significance (MGUS), chronic lymphocytic leukemia (CLL), mantle cell lymphoma, Burkitt's lymphoma, B-cell acute lymphoblastic leukemia, chronic myeloid leukemia, B-cell non-Hodgkin lymphoma, or diffuse large B-cell lymphoma. Preferably the disease is multiple myeloma.

Furthermore the disease to be treated can be a disease associated with overexpression of CD147 and/or MCT1 compared to the respective expression in healthy tissue, wherein the subject is resistant to IMiD treatment. Another term for such a disease is IMiD refractory disease. The resistance to IMiDs can be an inherent resistance or a resistance acquired during IMiD treatment. IMiD resistance can be assessed by the methods of the present invention.

A combination of an IMiD and an inhibitor of CD147 and/or MCT1 for the purpose of the description of the present invention encompasses any treatment regimen, wherein both the IMiD and the inhibitor are for administration to the subject to be treated. The invention also comprises the combination of CD147/MCT1 inhibitors for use in treating an IMiD refractory disease in a patient.

The inhibitor for use in treating a patient according to the invention will normally be for oral, parenteral, intravenous, intramuscular, subcutaneous, buccal, rectal, vaginal, transdermal administration and/or for administration via the nasal route and/or via inhalation.

The combination for use according to the present invention can also be in the form of a pharmaceutical composition comprising the active ingredient or a pharmaceutically acceptable salt thereof, in a pharmaceutically acceptable dosage form. Depending upon the disease to be treated and the individual patient to be treated and the route of administration, the compositions may be administered at varying doses.

Exemplary treatment regimens can be according to already approved treatment regimens concerning the IMiD, wherein additionally the inhibitor of MCT1 and/or the inhibitor of CD147 is for administration simultaneously, consecutively, or only sporadically. Specifically this encompasses treatment regimens, wherein with every dosage of IMiD, a dosage of the inhibitor is applied, or wherein only the initial dosage of IMiD is accompanied by a dosage of the inhibitor, or wherein the IMiD and the inhibitor are for intermittent and/or alternating application. The dosage regimen can encompass daily, weekly, or monthly intervals between the single application of the inhibitor and/or the IMiD. All this applies also to the application of the inhibitor or combination of inhibitors without IMiD application for use in treating an IMiD refractory disease.

Suitable daily doses of an inhibitor for use in the therapeutic treatment of humans according to the methods of the invention can be about 0.001-10 mg/kg body weight, preferably 0.01-3 mg/kg body weight.

Oral formulations are preferred particularly tablets or capsules which may be formulated by methods known to those skilled in the art to provide doses of the active compounds in the range of 0.5 mg to 500 mg for example 1 mg, 2 mg, 4 mg, 6 mg, 10 mg, 15 mg, 20 mg, 25 mg, 50 mg, 100 mg and 300 mg.

EXAMPLES

Example 1: Cell Culture and Drug Treatment

Cell Lines

HEK 293T and HeLa cells were grown in Dulbecco's modified Eagle's medium (DMEM), each media containing 10% fetal bovine serum (FBS). The human multiple myeloma cell lines MM1. S, U266, KMS-12-BM, RPMI 8226 and JJN3 were cultured in RPMI-1640 with 10% FBS. Where indicated, Lenalidomide or Pomalidomide (both Selleck Chemicals) were used at the indicated concentrations. Sf9 insect cells (Life technologies) were cultured in Sf-900 II serum-free medium (SFM, Life technologies) supplemented with 10% heat-inactivated FBS and 10 µg/ml gentamycin. High Five cells (Invitrogen) were cultured in Express Five SFM supplemented with 10 mM L-glutamine and 10 µg/ml gentamycin. All cells tested mycoplasma negative by a PCR detection method.

Primary $CD34^+$ MDS Cells

Mononuclear cells from bone marrow aspirates were enriched for $CD34^+$ cells by magnetic bead selection (MACS, MiltenyiBiotech) according to the manufacturer's instructions. $CD34^+$ cells were differentiated along the erythroid lineage essentially as known in the art. Briefly, viable cells were seeded into 12-well plates in 2 ml serum free medium (SFM) containing 80% IMDM Glutamax I (Gibco, Life Technologies), 20% BIT9500 (StemCell Technologies), 100 ng/ml kit ligand (KL), 100 ng/ml FLT3-Ligand (FL), 25 ng/ml TPO, 10 ng/ml IL3, 10 ng/ml IL6 and DMSO or 10 µM lenalidomide, respectively. On day 7, 2 IU/ml erythropoietin (EPO Janssen-CILAG GmbH) was added to the cultures to stimulate erythropoiesis. Half medium changes were performed every third day and cells were harvested on day 14.

Example 2: Analysis of CRBN Interactors

To identify interactors of CRBN, HEK293 cells were grown ($2 \times 10^9$ cells) in an adherent culture system for large-scale protein production. Cells were transfected with a CRBN-tandem-Strep-FLAG-tagged (CRBN-SF-TAP) construct, a non-tagged CRBN overexpression construct or SF-TAP empty vector. First, CRBN was precipitated with streptactin superflow resin (IBA). CRBN interacting proteins were eluted twice using desthiobiotin elution buffer (IBA). The eluate was then subjected to a second precipitation with anti-FLAG resin (anti-FLAG-M2-agarose, Sigma) and then subjected to a further competition with FLAG peptide (Sigma). Peptides generated by in-gel trypsin digestion were dried down and dissolved in 0.1% FA. LC-MS/MS was performed by coupling a nanoLC-Ultra (Eksigent) to a LTQ Orbitrap XL mass spectrometer (ThermoFisher Scientific), using a 60 min gradient from 0 to 40% solution B (0.1% FA in AcN) as described [10]. Mass spectra were analyzed using the flexAnalysis software (version 3.3) (Bruker Daltonik). Proteins were filtered using a minimal protein identification probability of 99% and minimal peptide identification probability of 95%.

Sequences of identified unique peptides corresponding to CD147 and MCT1 are shown in the following tables.

| | CD147 - P35613 | | | |
|---|---|---|---|---|
| Sequence | Mascot Ion score | Modifications | Start | Stop |
| (K)GGVVLKEDALPGQK(T) SEQ ID NO: 19 | 88.64 | | 58 | 71 |
| (K)EDALPGQK(T) SEQ ID NO: 20 | 58.06 | | 64 | 71 |
| (K)SSEHINEGETAMLVcK(S) SEQ ID NO: 21 | 78.3 | Carbamidomethyl (+57) | 112 | 127 |
| (K)SESVPPVTDWAWYK(I) SEQ ID NO: 22 | 56.25 | | 128 | 141 |
| (R)FFVSSSQGR(S) SEQ ID NO: 23 | 41.36 | | 158 | 166 |
| (R)SELHIENLNmEADPGQYR(C) SEQ ID NO: 24 | 87.48 | Oxidation (+16) | 167 | 184 |
| (K)GSDQAIITLR(V) SEQ ID NO: 25 | 66.62 | | 192 | 201 |
| (R)RKPEDVLDDDDAGSAPLK(S) SEQ ID NO: 26 | 83.3 | | 233 | 250 |

| | MCT1 - P53985 | | | |
|---|---|---|---|---|
| Sequence | Mascot Ion score | Modifications | Start | Stop |
| (K)SITVFFK(E) SEQ ID NO: 27 | 40 | | 39 | 45 |
| (K)DLHDANTDLIGRHPK(Q) SEQ ID NO: 28 | 55.97 | | 225 | 239 |
| (K)DLHDANTDLIGR(H) SEQ ID NO: 29 | 81.49 | | 225 | 236 |
| (R)LNDMYGDYK(Y) SEQ ID NO: 30 | 54.99 | | 412 | 420 |
| (K)KESKEEETSIDVAGKPNEVTK(A) SEQ ID NO:31 | 61.98 | | 459 | 479 |
| (K)ESKEEETSIDVAGKPNEVTK(A) SEQ ID NO: 32 | 52.8 | | 460 | 479 |

Example 3: Antibodies

Mouse monoclonal antibodies were purchased from Invitrogen (CUL1-2H4C9: #32-2400), Sigma (FLAG-M2: #F3165, β-actin: #A-1978), Covance (HA-16B12: #MMS-101P) and Santa Cruz (CD147 8D6: #sc-21746). Rabbit polyclonal antibodies were from Millipore (MCT1: #AB-3538P), Bethyl (DDB1: #A300-462A, CUL4A: #A300-739A), Sigma (FLAG, #F7425), Cell Signaling (α/β-tubulin: #2148, IKZF1: #5443, IKZF3: #12720), Proteintech (CUL4B: #12916-1-AP) and Santa Cruz (HA Y-11: #sc-805. A polyclonal antibody against CRBN was generated by immunizing rabbits with a mixture of two peptides containing amino acids 1-19 and 424-437 of human CRBN (MAGEDQQDAAHNMGNHLPC (SEQ ID NO: 1) and CPTIDPTEDEISPDK (SEQ ID NO: 2), respectively). Secondary antibodies (anti-rabbit IgG, anti-mouse IgG or protein-A coupled with horseradish peroxidase) were from GE Healthcare. Secondary antibodies (anti-rabbit IgG and anti-mouse IgG) coupled to Alexa Fluor 594 or Alexa Fluor 488 for immunofluorescence and flow cytometry were from Life technologies.

Example 4: Cell Lysis, Immunoprecipitations, and Immunoblotting

Cell samples were lysed in lysis buffer (NaCl 150 mM, Tris-HCl 50 mM, MgCl2 5 mM, EDTA 1 mM, NP-40 0.1%, Glycerol 5% and inhibitors) for whole cell lysates, immunoprecipitations or pulldown experiments. Details of extract preparation, immunoprecipitation, and immunoblotting were previously described [10]. Briefly, the cellular lysates were centrifuged 15 min at 14,000 rpm at 4° C. to separate from cellular debris. Protein concentration in the supernatants was measured before Laemmli buffer was added. The lysates were separated by SDS-PAGE and blotted onto PVDF (polyvinylidene difluoride) membranes. After blotting, PVDF membranes were stained with Ponceau solution to evaluate protein loading. After washing and blocking unspecific bindings in 5% milk, the membranes were incubated with primary antibodies. After addition of horseradish peroxidase coupled secondary antibodies, western blot membranes were developed using the ECL (enhanced chemoluminescence) method (SuperSignal West reagents from Thermo Scientific). For immunoprecipitations (IPs), cell lysates were incubated with Flag-M2 agarose beads (Sigma) for Flag-IPs, HA-7 agarose beads (Sigma) for HA-IPs, or protein-A sepharose beads (GE Healthcare) together with primary rabbit antibodies for binding of endogenous proteins (e.g. for CRBN-IP). For the experiments using a protein cross linker, DSS (Pierce) was added to the cells to a final concentration of 1 mM for 45 minutes at RT. The Cross linker was quenched by addition of Tris-HCl, pH 7.5 20 mM and cell lysis was performed as described, with the only exception of HEPES buffer 50 mM, pH 7.5 instead of Tris-HCl buffer. After washing the beads four times in lysis buffer, Laemmli buffer was added and proteins were analyzed by SDS-electrophoresis.

Example 5: Plasmids and Small Hairpin RNAs cDNAs of CRBN, CD147 (isoform 2) and MCT1 as well as the IMiD-binding defective mutant of CRBN ("CRBN YW"=CRBN Y384A and W386A) were cloned without tag or with HA- or Flag-tag into the expression plasmids pcDNA 3.1 (Life technologies) or pcDNA-C-SF-TAP, respectively. cDNAs of CRBN, DDB1, CUL4A and ROC1 were cloned (with or without His- or FLAG-tag) into the baculoviral expression vector pBacPAK9 (Clontech). Full-length CRBN and the intracellular domains of MCT1 (middle loop amino acids 188-262 and C-terminus amino acids 444-500) and CD147 (C-terminus amino acids 230-269) were cloned into the pGEX-4T2 expression vector. All cDNAs were sequenced. For shRNA mediated silencing of CRBN, CD147, MCT1, IKZF1 or IKZF3, specific shRNAs were cloned into the pIKO.1 plasmid (Addgene) in which the puromycin resistance cassette was replaced by the cDNA coding for DsRed-Express2, a red fluorochrome.

The shRNA target sequences were:

```
for CRBN:
                                    (SEQ ID NO: 3)
(#1) 5'-CGCTGGCTGTATTCCTTATAT-3'

(SEQ ID NO: 4)
(#2) 5'-CCAGAAACATCTACTTGGGTA-3' for CD147:
                                    (SEQ ID NO: 5)
5'-GTACAAGATCACTGACTCTGA-3' for MCT1:
                                    (SEQ ID NO: 6)
5'-GCAGGGAAAGATAAGTCTAAA-3' for IKZF1:
                                    (SEQ ID NO: 7)
5'-CTACGAGAAGGAGAACGAAAT-3' for IKZF3:
                                    (SEQ ID NO: 8)
5'-GCCTGAAATCCCTTACAGCTA-3' for CUL4A:
                                    (SEQ ID NO: 33)
5'-GCAGAACTGATCGCAAAGCAT-3', for CUL4B:
                                    (SEQ ID NO: 34)
5'-GCCATGAAAGAAGCATTTGAA-3' for control / sh_scramble:
                                    (SEQ ID NO: 9)
5'-CCTAAGGTTAAGTCGCCCTCG-3'
```

Example 6: Transient Transfections, Production of Lentiviral Particles and Lentivirus-Mediated Dna Transfer HEK 293T cells were transfected using the calcium phosphate method, HeLa cells were transfected with Lipofectamine transfection reagent (Invitrogen) according to the manufacturer's instructions. For lentivirus production, HEK 293T cells were transfected with shRNA encoding pIKO.1 plasmids or, for overexpression, pHIV.EGFP based constructs, together with the envelope plasmid pMD2.G (Addgene) and the packaging plasmid psPAX2 (Addgene). 48 hours after transfection, the virus-containing medium was collected and supplemented with 8 µg/ml polybrene (Sigma).

For infection, MM cells lines or HeLa cells were plated in 6 well plates and incubated with the virus-containing supernatant (containing polybrene) for 24 hours. At the beginning of the incubation time, spin infection was performed once at 1000 rpm for 30 min at 32° C.

Example 7: Purification of GST-Tagged Protein Fragments from BL21 Bacterial Cells The intracellular domains of MCT1 (middle loop and C-terminus) and CD147 (C-terminus) were cloned into the pGEX-4T2 expression vector and transformed into BL21 competent *E. coli* cells. 3.5 hours after induction of recombinant protein expression with IPTG, bacteria were harvested. After lysis in NETN buffer (NaCl 100 mM, Tris-HCl 20 mM, EDTA 1 mM, NP-40 0.5%, PMSF 2 mM and inhibitors), the bacterial suspension was sonicated and centrifuged at 9500 rpm to remove debris. Supernatants were incubated with glutathione sepharose 4B (Amersham Biosciences) beads for 1.5 hours, before beads were washed repeatedly. The beads with the bound purified GST-fusion proteins were stored in NETN buffer.

Example 8: Lactate Measurement

For analysis of intra- and extracellular lactate, lenalidomide or DMSO treated cells were centrifuged down. For extracellular lactate, the supernatant was collected and frozen; normal cell culture medium was used as control for normalization. For measurement of intracellular lactate, cell pellets were lysed in lysis buffer. Lactate content in cell lysates as well as in the supernatants were analysed with the cobas 8000 (Roche).

Example 9: Immunofluorescence

Immunofluorescence was performed as described [10]. Briefly, HeLa cells stably expressing sh_CRBN or sh_scramble were grown on glass coverslips and transfected with constructs expressing HA-CD147 and/or Flag-MCT1 using Lipofectamine (Invitrogen). Primary antibodies were anti-HA (mouse) and anti-FLAG (rabbit). Alexa Fluor 488 conjugated anti-rabbit and Alexa Fluor 594 conjugated anti-mouse (Invitrogen) were used as secondary antibodies. DAPI was used to counterstain DNA. Where indicated, ER tracker blue white DPX (Life technologies) was added to cells in culture for 30 min before fixation. Images were taken using the laser-scanning confocal microscope FluoView FV10i (Olympus). For quantification, 100 cells for each condition were analyzed in three independent experiments.

Example 10: mRNA Expression in Cell Lines

For quantification of CRBN, CD147, MCT1, and ARPP P0 mRNA expression, MM cell lines with or without IMiD treatment, total RNA was extracted using the RNeasy Kit (Qiagen). cDNA synthesis was performed using Superscript III (Invitrogen). Quantitative PCR analysis (SYBR Green) was performed according to standard procedures. ARPP (acidic ribosomal phosphoprotein P0) was used as internal reference. Primer sequences were:

```
CRBN:
                                       (SEQ ID NO: 10)
5'-ACAGCTGGTTTCCTGGGTATGC-3'
and
                                       (SEQ ID NO: 11)
5'-ACAGAGCAGATCGCGTTAAGCC-3'
MCT1:
                                       (SEQ ID NO: 12)
5'-TGGCTGTCATGTATGGTGGAGGTC-3'
and
                                       (SEQ ID NO: 13)
5'-GAAGCTGCAATCAAGCCACAGC-3'
CD147:
                                       (SEQ ID NO: 14)
5'-GATCACTGACTCTGAGGACAAGGC-3'
and
                                       (SEQ ID NO: 15)
5'-TGCGAGGAACTCACGAAGAACC-3'
ARPP:
                                       (SEQ ID NO: 16)
5'-GCACTGGAAGTCCAACTACTTC-3'
and
                                       (SEQ ID NO: 17)
5'-TGAGGTCCTCCTTGGTGAACAC-3'
```

For verification of efficient CD147 knock-down in zebrafish embryos, total RNA of larvae injected with CD147 splice morpholino or control was extracted using the QIAshredder and RNeasy Kit (both Qiagen); cDNA synthesis was performed as described above. PCR reactions were performed on the peqSTAR2x gradient thermocycler (Peqlab) following standard procedures and using the following primers:

```
for CD147:
                                       (SEQ ID NO: 35)
5'-AGGCCACTATTGGGTCAAGAATGGAAAGAAAATC-3' (exon 3),
and
                                        SEQ ID NO: 36)
5'-CCGTTCTCCTGCATCAGGAAGCTTGAAC-3' (exon 5)

for β-actin :
                                       (SEQ ID NO: 37)
5'-TGTTTTCCCCTCCATTGTTGG-3'
and
                                       (SEQ ID NO: 38)
5'-TTCTCCTTGATGTCACGGAC-3'.
```

One fifth of the PCR reaction was loaded onto an agarose gel and subjected to gel electrophoresis.

Example 11: Flow Cytometry

MM Cells

MM1. S cells were treated with Lenalidomide or DMSO for 72 hours and then incubated with mouse anti-CD147 antibody (Santa Cruz) or $IgG_{2a}$ control isotype antibody (Bethyl). The secondary antibody was FITC-coupled anti mouse IgG. After washing, stained cells were analysed for CD147 expression using a FACSCalibur (Becton Dickinson).

MDS Bone Marrow Samples

After informed consent, bone marrow samples from patients with MDS were collected in heparin, lysed with Versalyse® (Beckman Coulter, Krefeld, Germany), stained with anti-human monoclonal fluorochrome-conjugated antibodies and analyzed by flow-cytometry on a Cytomics FC 500 analyzer (Beckman Coulter). The following antibodies were used: Beckman Coulter: CD45-ECD (clone J33), CD33-PE (clone D3HL60.251), CD14-PECy5 (clone RM052), CD7-PE (clone 8H8.1), CD3-PECy5 (clone UCHT1), CD19-PECy7 (clone J4.119), CD7-PE, GlyA-PE (clone 11E4B-7-6), CD34-PECy7 (clone 581) and CD147-FITC (clone HIM6) from BD Biosciences. Using a CD45 vs. SSC gating strategy monocytes, lymphocytes, granulocytes, progenitor cells and CD45low/-GlyA+ cells were identified. Gates were then placed on CD19+ B-cells, CD3+ T-cells and CD3-CD7+ NK cells within the lymphocyte gate; on CD33+ granulocytes and CD14+ monocytes; on CD45lowCD33+ CD34+ progenitor cells and on CD45low/-GlyA+ erythropoiesis. CD147 expression of CD45low/-GlyA+ erythropoiesis was then determined by histogram gating. Data are represented as median fluorescence intensity of CD147 relative to isotype-matched control. Data were analyzed using Kaluza® Flow Analysis Software (Beckman Coulter).

In Vitro Propagated MDS Progenitor Cells

Cells were collected and washed with Annexin/PI buffer containing 1M Hepes, 2.5 M NaCl, 1.62 mM $CaCl_2$. Cell pellets were stained with CD34-FITC (BD Pharmingen, clone 581/CD34), CD147-PE (BD Pharmingen, clone HIM6), CD33-PC5.5 (Beckmann Coulter, clone D3HL60.251), CD45 PE Cy7 (eBioscience, clone HI30), CD36-APC Cy7 (BioLegend, clone 336213), primary CD235α-biotin (eBioscience, clone HIR2) and secondary streptavidin eFluor®450 (eBioscience) antibodies according to manufacturer's instructions. The combination of APC Annexin V (BD Pharmingen) and PI was added for the determination of apoptosis and necrosis. Single stained samples were used for compensation.

Flow cytometry was performed on a CyAn ADP LxP8 (Coulter-Cytomation) and data were analyzed using FlowJo software (TreeStar Inc.).

Example 12: Zebrafish Experiments

Briefly, Zebrafish larvae were injected with different concentrations of splice-Morpholinos targeting all 3 predicted CD147 isoforms in zebrafish or treated with 400 µM Thalidomide on the day of fertilization. On day 1 and 3 after fertilization, the phenotypes of the larvae were analysed.

The wildtype strain AB was used in all experiments. All embryos were kept at 28.5° C. in E3 media (5 mM NaCl, 0.17 mM KCl, 0.33 mM $CaCl_2$, 0.33 mM $MgSO_4$) supplemented with $10^{-5}$% methylene blue. All experiments were performed in accordance with animal protection standards of the Ludwig-Maximilians University Munich and were approved by the government of Upper Bavaria (Regierung von Oberbayern, Munich, Germany).

Knock-down of CD147 in zebrafish was done by microininjection of 2-4 µl of 0.1 mM or 0.25 mM antisense morpholino oligo (Gene Tools, LLC) targeting either a splice junction of CD147 (CD147 splice MO; exonic sequence in upper case: 5'-aagaggtgaagaacatacAAGTGTT-3' (SEQ ID NO: 18) or the ATG start codon (CD147 ATG MO; 5'-GCGCCAAAGAGCTTCTTTTCCATGC-3' (SEQ ID NO: 39) at the 1 cell stage. Injected eggs and controls were cultured at 28° C. in E3 buffer. For each experiment, 50 eggs were injected.

For thalidomide treatment, fertilized embryos were randomly split into two groups at 3 hours post fertilization (hpf): One group was transferred into E3 containing 0.1% DMSO, the other group into E3 with 400 µM thalidomide (Sigma-Aldrich) and kept at 28.5° C. for 3 days.

Larvae were analyzed for phenotypes at 3 days post fertilization (dpf). For each experiment, 10 embryos were treated. CD147 splice MO-injected larvae were compared to control larvae and thalidomide treated larvae were compared to DMSO controls. Larvae were anesthetized with Tricaine (0.016% w/v) and mounted in 3% methylcellulose on coverslips. DIC images were taken with an Axioplan2 compound microscope (Zeiss).

Example 13: Recombinant Proteins and GST-Affinity Purifications

GST fusion proteins were purified from *E. Coli* BL21 cells after induction with isopropyl-8-D-thiogalactopyranoside (IPTG) in NETN buffer (NaCl 100 mM, Tris-HCl 20 mM, EDTA 1 mM, NP-40 0.5%, PMSF 2 mM and protease inhibitors). For GST pulldown experiments (investigating binding of protein fragments of MCT1 and CD147 to human CRBN), cell lysates were incubated with the GST-tagged MCT1 and CD147 fragments bound to glutathione sepharose 4B beads (Amersham Biosciences). Pre-cleared mammalian cell lysates were incubated with empty glutathione sepharose 4B beads or GST-purified proteins for 1.5 hours. For IVT assays, purified GST-Cereblon was incubated with $^{35}$S-labeled, in vitro-translated CD147 or MCT1 in binding buffer (1×phosphate-buffered saline [PBS], 0.1% NP-40, 0.5 mM dithiothreitol [DTT], 10% glycerol, supplemented with protease inhibitors). In vitro translation was done with the TNT T7 quick-coupled transcription/translation system (Promega Corporation, Madison, Wis.) following the manufacturer's instructions. Recombinant CRBN, DDB1, CUL4A, ROC1 were produced in High Five insect cells and purified as previously described [10].

Example 14: In Vitro Ubiquitylation Assay

The ubiquitylation of IKZF3, CD147 and MCT1 was performed with conditions previously described with slight modifications [1,2]. Briefly, FLAG-IKFZ3, FLAG-CD147 or FLAG-MCT1 substrates were purified from 293T cells and ubiquitylation reactions were performed in presence or absence of lenalidomide 10 µM, at 30° C. in a total volume of 12 µl containing 50 mM Tris at pH 7.6, 5 mM MgCl2, 0.6 mM dithiothreitol, 2 mM ATP, 1.5 ng µl-1 E1 (Boston Biochem), 10 ng/µl Ubc3, 10 ng/µl Ubc5a and Ubc5b, 2.5 µg/µl ubiquitin (Sigma), 1 µM ubiquitin aldehyde, and approximately 1 µg each of purified CRL4$^{CRBN}$ E3 ligase complex purified from High five insect cells.

Example 15: Pulse Chase Analysis

In a complementary approach using pulse-chase analysis, CD147 protein maturation from the immature core-glycosylated to the mature high-glycosylated form necessary for membrane localization was investigated. Indeed, CD147 glycosylation as a readout for maturation and membrane localization was substantially impaired upon lenalidomide treatment or CRBN silencing, while no effect was observed on CD147 de novo synthesis (FIG. 13H,I; FIG. 21D). Importantly, treatment with MLN4924, an inhibitor of Cullin-RING ubiquitin ligases, had no effect on CD147 stability or processing, thereby further underscoring a ubiquitin-independent effect of CRBN on CD147 (FIG. 13h). These data suggest that CD147 and MCT1 depend on CRBN for proper maturation, complex assembly and membrane localization, thereby implying a chaperone-like function of CRBN for CD147 and MCT1.

Labelling of MM1S cells with $^{35}$S-Met/Cys was essentially performed as described previously [10]. Briefly, MM1S cells that were either infected with CRBN shRNA constructs or treated with lenalidomide, were washed three times with PBS and incubated in methionine- and cysteine-free DMEM for 1 hour. Newly translated proteins were metabolically labeled for 45 minutes with methionine- and cysteine-free DMEM containing 0.2 mCi/ml [35S]-Met/Cys. Cells were then washed three times with PBS (37° C.) and incubated with DMEM for up to 24 hours. For experiments testing the effect of lenalidomide, exposure to the drug was ascertained throughout all steps.

Example 16: Cell Proliferation

MM cells were subjected to treatment with lenalidomide/DMSO for the indicated times or infected with lentiviral-shRNA. On days indicated, proliferation was assessed using the trypan blue exclusion method. Results are presented as ratios to DMSO, wildtype or sh_scramble controls.

Example 17: VEGF and MMP7 Secretion

For analysis of VEGF and MMP7 in cell culture supernatants, lenalidomide/DMSO or lentiviral-sh pretreated MM cells were incubated for 3 h in fresh medium. Supernatants were collected and snap-frozen for subsequent analysis. VEGF and MMP7 concentrations were determined in an enzyme linked immunosorbent assay (ELISA) using kits RAB0507 and RAB0369 (VEGF and MMP7 respectively, both Sigma) according to the manufacturer's instructions. Results were normalized to protein concentration of corresponding cell lysates.

Example 18: Statistical Analysis

Statistical analyses of the results were performed by Student's t test or one-way ANOVA, according to assumptions of the test, using GraphPad Prism software. Statistical analysis of relative ratios was performed using one-sample t-tests with hypothetical means of 1.0. The error bars shown in the figures represent the mean±S.D. The P values are presented in the figure legends where a statistically significant difference was found: *, $P<0.05$; , $P<0.01$; *, $P<0.001$; ****, $P<0.0001$.

Example 19: Further Studies on Interaction Between CRBN and MCT1 and CD147

To further investigate the possibility that CRBN regulates CD147 and MCT1 in a ubiquitin-independent fashion, CUL4A and CUL4B, the core scaffold proteins of the CRL4$^{CRBN}$ ligase complex, were depleted to inhibit CRBN associated ubiquitylation activity. Contrary to CRBN silencing (FIG. 12B; FIG. 16C), knock-down of CUL4A/B had neither an effect on the overall stability of CD147 and MCT1 nor on the lenalidomide induced destabilization of both proteins (FIG. 12g). Likewise, the purified CRL4$^{CRBN}$ ligase complex was unable to ubiquitylate CD147 and MCT1 in a reconstituted in vitro ubiquitylation approach (FIG. 20A). In addition, CUL4A-immunoprecipitates failed to retrieve CD147 and MCT1, suggesting that CRBN forms a CRL4-independent complex with CD147 and MCT1 (FIG. 20B).

Given the stabilizing effect of CRBN on CD147 and MCT1 and the presence of a large LON domain in CRBN, which is typically shared by proteases and chaperones, the possibility that CRBN behaves like a chaperone necessary for maturation of the CD147/MCT1 complex was contemplated. First, it was determined whether CRBN depletion results in subcellular mislocalization or aggregation of the complex. Indeed, silencing of CRBN substantially decreased expression of CD147 and MCT1 at the cell membrane, while we observed accumulation of both proteins at the endoplasmatic reticulum (FIG. 13A-E; FIG. 21A). Likewise, lenalidomide treatment decreased CD147 cell surface expression (FIG. 21B). To determine if CRBN acts at an early stage of maturation, both CD147 and MCT1 were isolated from HEK293T cells treated with cycloheximide to block translation. CRBN was recovered in CD147 and MCT1 immunoprecipitates from control cells (FIG. 13F,G). This interaction was progressively lost upon inhibition of translation, while instead, increased association between CD147 and MCT1 was observed over time (FIG. 13F,G). Consistent with the binding to freshly translated CD147/MCT1, CRBN was found to preferentially interact with the immature, core-glycosylated form of CD147 (FIG. 12A), and progressive accumulation of this immature form upon lenalidomide-treatment was observed (FIG. 12V). Likewise, induced expression of CRBN promoted complex formation of CD147 and MCT1 (FIG. 21C).

Next, it was attempted to determine whether IMiDs mediate their specific biological and therapeutic effects via destabilization of the CD147/MCT1 complex. Different MM cell lines with described lenalidomide-sensitivity (MM1S, U266) or -resistance (KMS12BM, RPMI 8226) regarding changes in CD147 and MCT1 stability upon IMiD treatment were examined. Strikingly, destabilization of CD147 and MCT1 upon lenalidomide exposure was only observed in lenalidomide-sensitive lines while expression in resistant MM lines remained unchanged (FIG. 14A,B; FIG. 22). Knock-down of CD147 and MCT1 by RNAi substantially attenuated proliferation in both lenalidomide-sensitive and -resistant MM cell lines (FIG. 14C; FIG. 22B), Importantly, induced overexpression of CD147 and MCT1 attenuated the anti-myeloma effect of lenalidomide in sensitive cells, providing a functional link to CD147/MCT1 (FIG. 14D,E). Of further notice, lenalidomide-resistant lines nevertheless show IKZF3 destruction upon treatment, further supporting the notion that MCT1/CD147 are important targets (FIG. 14B).

The various pro-survival and pro-proliferative effects of the CD147/MCT1 complex include the induction of matrix metalloproteinases (MMPs) and VEGF, which favor invasion and angiogenesis, and the export of lactate, which allows for an increased use of the glycolytic pathway, as typically observed in malignant cells. In line with destabilization of the CD147/MCT1 complex, lenalidomide treatment significantly reduced VEGF and MMP7 secretion and gave rise to significantly elevated intracellular lactate levels in lenalidomide-sensitive MM cell lines, while only minor effects were observed in resistant MM cell lines (FIG. 14F-H). Likewise, elevated intracellular lactate levels and decreased VEGF secretion were observed upon RNAi induced silencing of CRBN (FIG. 14I,J).

Next to their prominent role in the treatment of B-cell neoplasms like MM, IMiDs demonstrate high response rates in other malignancies as MDS with deletion of chromosome 5q [del(5q) MDS], a myeloid malignancy, where lenalidomide but also thalidomide are clinically effective (pomalidomide remains to be tested for MDS treatment). In order to evaluate the importance of CD147/MCT1 in this entity, CD147 surface expression in primary human del(5q) MDS samples from patients either before or on lenalidomide treatment were assessed, and compared to samples of patients with non-del(5q) MDS, which is far less responsive to lenalidomide treatment. Of note, del(5q) MDS is clinically characterized by a profound macrocytic anemia, and lenalidomide restores normal erythropoiesis in this disease by inhibiting growth of del(5q) erythroid progenitors. Significantly elevated CD147 surface expression in the erythropoietic compartment of del(5q) MDS samples was found, which was attenuated to the level of non-del(5q) MDS samples upon lenalidomide treatment and achievement of remission (FIG. 15A; and see Table below).

Table showing MDS patients' characteristics.

| Patient | sex | age | WHO subtype | cytogenetics | IPSS | Under lenalidomide treatment |
|---|---|---|---|---|---|---|
| 1 | m | 57 | RAEB1 | 46 XY t(8; 10) | INT1 | |
| 2 | m | 72 | RAEB1 | 47, XY, +8 | INT1 | |
| 3 | w | 58 | RAEB1 | 46 XX | INT1 | |
| 4 | w | 70 | RAEB1 | 46 XX | INT1 | |
| 5 | w | 67 | RARS | 46 XX | low | |
| 6 | w | 71 | RCMD | 46 XX | INT1 | |
| 7 | m | 74 | RCMD | 46 XY | INT1 | |
| 8 | m | 74 | RCMD | 46, XY | low | |
| 9 | m | 66 | RAEB1 | 46 XY | INT1 | |
| 10 | w | 42 | RCMD-RS | 46 XX | low | |
| 11 | w | 60 | RA | 46 XX | low | |
| 12 | w | 73 | RCMD | 46 XX, del(5q) | INT1 | |
| 13 | w | 79 | RCMD | 46 XX del(5q) | low | |
| 14 | w | 72 | RCMD | 46 XX del(5q) | low | |
| 15 | w | 74 | RCMD | 46 XX del(5q) | low | |
| 16 | m | 72 | RCMD | 46 XY, del(5q) | low | |
| 17 | w | 79 | RCMD | 46 XX del(5q) | low | |
| 18 | w | 74 | RCMD | 46 XX del(5q) | low | |
| 19 | m | 69 | RCMD | 46 XY del(5q) | low | |
| 20 | w | 72 | RCMD | 46 XX del(5q) | low | |
| 21 | w | 74 | RCMD | 46 XX del(5q) | low | |
| 22 | m | 65 | RAEB1 | 46, XX del(5q), −7 | INT2 | |
| 23 | m | 68 | RCMD | 46, XY del(5q) | low | |
| 24 | w | 82 | RAEB1 | 46, XX del(5q) | INT1 | x |
| 25 | w | 65 | RCMD | 46, XX del(5q) | low | x |
| 26 | w | 67 | RCMD | 46 XX del(5q) | low | x |
| 27 | w | 80 | RCMD | 46 XX del(5q) | low | x |
| 28 | w | 52 | RCMD | 46, XX del(5q) | low | x |
| 29 | w | 77 | RCMD | 46, XX del(5q) | low | x |
| 30 | w | 79 | RCMD | 46 XX del(5q) | low | x |
| 31 | w | 72 | RCMD | 46 XX del(5q) | low | x |
| 32 | w | 73 | RCMD | 46 XX del(5q) | low | x |
| 33 | w | 54 | RAEB1 | 46 XX del(5q) | INT1 | x |

RCMD, refractory cytopenia with multilineage dysplasia; RCMD-RS, refractory cytopenia with multilineage dysplasia and ring sideroblasts; RAEB, refractory anemia with excess blasts IPSS, International Prognostic Scoring System; INT1, intermediate 1; INT2, intermediate To substantiate this finding and functionally link CD147 destabilization to the efficacy of lenalidomide in del(5q) MDS, bone marrow derived CD34$^+$ cells were propagated from untreated del(5q) MDS patients in vitro. Cells were treated with either lenalidomide or DMSO and stimulated with specific cytokines to induce erythroid differentiation (FIG. 15B). Indeed, lenalidomide-induced apoptosis was largely restricted to early erythroid cells (FIG. 15B,C). Importantly, cells with loss of CD147 surface expression underwent apoptosis, while cells maintaining CD147 expression were non-affected, supporting our hypothesis that lenalidomide eradicates the 5q-MDS clone by means of destabilizing CD147 (FIG. 15B,D).

Finally, a possible role of the CRBN-CD147/MCT1 axis in IMiD teratogenicity was investigated. To this end zebrafish was used as a model system, which has previously been successfully used to demonstrate the involvement of CRBN in IMiD teratogenicity. Notably, IMiDs are not teratogenic in rodents like mice and rats. Indeed, we could reproduce that thalidomide treatment of zebrafish results in a teratotoxic phenotype, including reduced size of head, fins, and eyes (FIG. 15E). Strikingly, morpholino-induced loss of CD147 phenocopied this teratotoxic effect in a dose dependent manner, and led to comparable reductions in head, fin, and eye size at 3 days post fertilization, suggesting that IMiDs mediate teratogenicity via CD147 destabilization (FIG. 15F; FIG. 23).

REFERENCES

[1] Kronke et al.: Lenalidomide causes selective degradation of IKZF1 and IKZF3 in multiple myeloma cells, Science, 343 (2014) 301-305.

[2] Lu et al.: The myeloma drug lenalidomide promotes the cereblon-dependent destruction of Ikaros proteins, Science, 343 (2014) 305-309.

[3] Zhu et al.: Cereblon expression is required for the antimyeloma activity of lenalidomide and pomalidomide, Blood, 118 (2011) 4771-4779.

[4] Greenberg et al.: Responsiveness of cytogenetically discrete human myeloma cell lines to lenalidomide: lack of correlation with cereblon and interferon regulatory factor 4 expression levels, Eur J Haematol, (2013).

[5] Gandhi et al.: Measuring cereblon as a biomarker of response or resistance to lenalidomide and pomalidomide requires use of standardized reagents and understanding of gene complexity, Br J Haematol, (2013).

[6] Broyl et al.: High cereblon expression is associated with better survival in patients with newly diagnosed multiple myeloma treated with thalidomide maintenance, Blood, 121 (2013) 624-627.

[7] Heintel et al.: High expression of cereblon (CRBN) is associated with improved clinical response in patients with multiple myeloma treated with lenalidomide and dexamethasone, Br J Haematol, (2013).

[8] Schuster et al.: The clinical significance of cereblon expression in multiple myeloma, Leuk Res, (2013).

[9] Niu et al.: Treatment of (131)I-labeled anti-CD147 monoclonal antibody in VX2 carcinoma-induced liver tumors, Oncol Rep. 2013 July; 30(1):246-52

[10] Fernandez-Saiz et al.: $SCF^{Fbxo9}$ and CK2 direct the cellular response to growth factor withdrawal via Tel2/Tti1 degradation and promote survival in multiple myeloma, Nature Cell Biology 15, 72-81 (2013)

The invention claimed is:

1. A pharmaceutical composition comprising:
   a) an immunomodulatory drug (IMiD) selected from the group consisting of thalidomide or a pharmaceutically acceptable salt thereof, and an analog of thalidomide or a pharmaceutically acceptable salt thereof; and
   b) an inhibitor of MCT1 or a pharmaceutically acceptable salt thereof.

2. The composition of claim 1, wherein the IMiD is selected from the group consisting of thalidomide, lenalidomide, and pomalidomide.

3. The composition of claim 1, further comprising a pharmaceutically acceptable excipient.

4. The composition of claim 1, wherein the inhibitor of MCT1 is selected from the group consisting of an antisense molecule, a small interfering RNA (siRNA), a protein, a peptide, an antibody, an antigenic fragment and a chemical compound.

5. A method of treating a disease associated with overexpression of MCT1 in a subject, as compared to expression in healthy tissue, comprising administering to the subject a composition comprising:
   a) an immunomodulatory drug (IMiD) selected from the group consisting of thalidomide or a pharmaceutically acceptable salt thereof, and an analog of thalidomide or a pharmaceutically acceptable salt thereof; and
   b) an inhibitor of MCT1 or a pharmaceutically acceptable salt thereof.

6. The method of claim 5, wherein the subject is resistant to IMiD treatment.

7. The method of claim 5, wherein the disease is a cancer or pre-malignant condition, wherein MCT1 is overexpressed.

8. The method of claim 7, wherein the cancer is selected from the group consisting of a solid cancer and a blood cancer or a hematological malignancy.

9. The method of claim 5, wherein the IMiD is selected from the group consisting of thalidomide, lenalidomide, and pomalidomide.

* * * * *